(12) United States Patent
Donohue et al.

(10) Patent No.: US 10,155,225 B2
(45) Date of Patent: Dec. 18, 2018

(54) AUTOMATED REAGENT MANAGER OF A DIAGNOSTIC ANALYZER SYSTEM

(71) Applicant: ABBOTT LABORATORIES, Abbott Park, IL (US)

(72) Inventors: Joseph P. Donohue, Pleasant Prairie, WI (US); Surya Pratap Rai, Gurnee, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 16/004,814

(22) Filed: Jun. 11, 2018

(65) Prior Publication Data

US 2018/0290140 A1 Oct. 11, 2018

Related U.S. Application Data

(62) Division of application No. 14/214,019, filed on Mar. 14, 2014, now Pat. No. 9,993,820.

(60) Provisional application No. 61/793,888, filed on Mar. 15, 2013.

(51) Int. Cl.
*B01L 3/00* (2006.01)
*G01N 35/10* (2006.01)
*B01L 9/00* (2006.01)
*G01N 35/00* (2006.01)

(52) U.S. Cl.
CPC .............. *B01L 3/52* (2013.01); *B01L 3/523* (2013.01); *B01L 9/50* (2013.01); *G01N 35/1002* (2013.01); *B01L 2200/023* (2013.01); *B01L 2200/025* (2013.01); *B01L 2300/041* (2013.01); *G01N 2035/00524* (2013.01)

(58) Field of Classification Search
CPC ............ B01F 2009/0092; G01N 1/286; G01N 35/1002; G01N 2035/00524
See application file for complete search history.

(56) References Cited

U.S. PATENT DOCUMENTS

| 6,299,567 B1 * | 10/2001 | Forrest | B01F 9/0018 366/220 |
| 6,440,371 B1 * | 8/2002 | Dumitrescu | B01F 13/002 422/430 |
| 2006/0263248 A1 * | 11/2006 | Gomm | G01N 35/025 422/63 |

(Continued)

*Primary Examiner* — Tony G Soohoo
*Assistant Examiner* — Elizabeth Insler
(74) *Attorney, Agent, or Firm* — Klintworth & Rozenblat IP LLP

(57) ABSTRACT

A reagent manager for a diagnostic analyzer system includes a reagent manager housing, a high-speed reagent bottle spinning device, a processor, and a memory. The reagent manager housing is for housing reagent bottles. The high-speed reagent bottle spinning device is disposed within the reagent manager housing for spinning at least one of the reagent bottles. The processor is in electronic communication with the high-speed reagent bottle spinning device. The memory is in electronic communication with the processor. The memory includes programming code for execution by the processor. The programming code is configured to spin the high-speed reagent bottle spinning device to spin the at least one reagent bottle to remove microparticles from a bottom surface of a septum of the at least one reagent bottle.

20 Claims, 18 Drawing Sheets

(56) References Cited

U.S. PATENT DOCUMENTS

2012/0218854 A1* 8/2012 Behringer ............... B01F 9/002
366/140

* cited by examiner

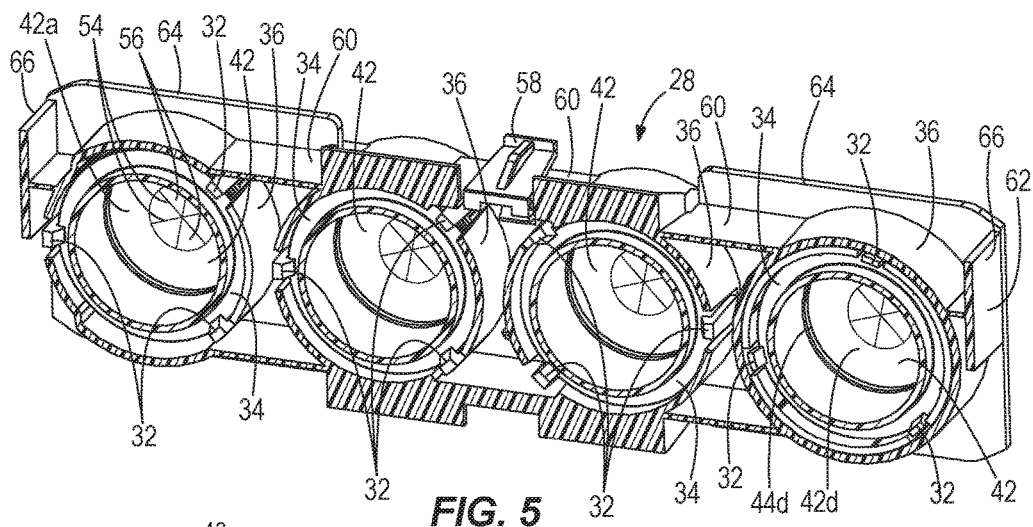
FIG. 5
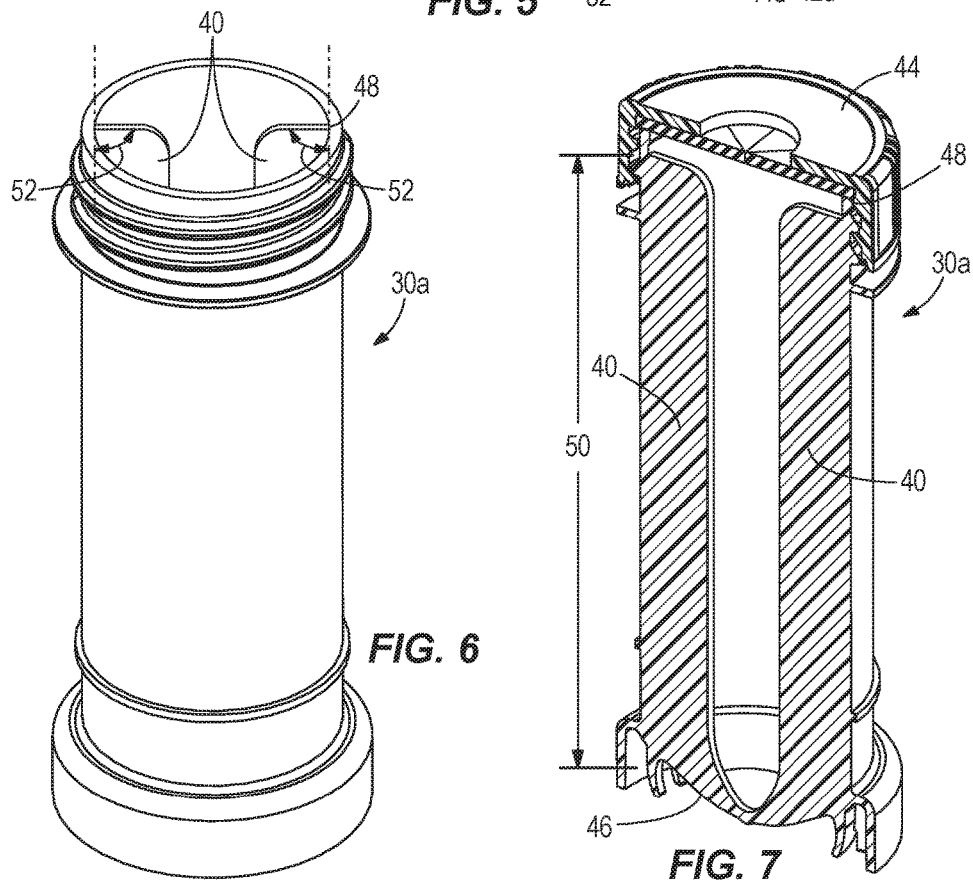
FIG. 6
FIG. 7

AUTOMATED REAGENT MANAGER OF A DIAGNOSTIC ANALYZER SYSTEM

CROSS-REFERENCE TO RELATED APPLICATIONS

This application is a Divisional of U.S. application Ser. No. 14/214,019 filed Mar. 14, 2014, which claims the benefit of U.S. provisional application No. 61/793,888, filed on Mar. 15, 2013, which are incorporated by reference in their entirety.

FIELD OF THE DISCLOSURE

This disclosure relates to reagent managers for diagnostic analyzer systems.

BACKGROUND

Reagent managers of diagnostic analyzer systems supply reagents to the diagnostic analyzer system for testing of samples. The reagents are typically shipped in reagent bottles. Upon arrival the reagent bottles may need to be manually prepared for insertion into the reagent manager. The manual preparation often involves a user flipping the reagent bottles between upside-down positions and right-side up positions a large number of times over a significant amount of time in order to remove microparticles which may be stuck on bottom surfaces of caps of the reagent bottles. Further, the manual preparation may involve replacing the caps of the reagent bottles with septum. Often the reagent bottles may have to be inserted into the reagent manager in a certain order. The manual preparation and the insertion of the reagent bottles into the reagent manager may take substantial time and effort. While the reagent manager is being loaded with new reagent bottles processing of the diagnostic analyzer system, using reagents in reagent bottles previously disposed within the reagent manager, may be temporarily stopped taking up time and decreasing through-put. Once the reagent bottles are disposed within the reagent manager, the reagent manager may not have a completely accurate reagent manager of tracking the reagent bottles. Moreover, the user may need to remain present after the reagent bottles have been inserted into the reagent manager in order to manually dispose of the reagent cartridges after they have been emptied by the reagent manager. All of this may take substantial time and effort on behalf of the user and may decrease through-put of the diagnostic analyzer system.

A reagent manager and reagent manager of operating a reagent manager is needed to overcome one or more of the issues of one or more of the existing diagnostic analyzer systems.

SUMMARY

In one embodiment, a reagent manager for a diagnostic analyzer system is disclosed. The reagent manager includes a reagent manager housing, a high-speed reagent bottle spinning device, a processor, and a memory. The reagent manager housing is for housing reagent bottles. The high-speed reagent bottle spinning device is disposed within the reagent manager housing for spinning at least one of the reagent bottles. The processor is in electronic communication with the high-speed reagent bottle spinning device. The memory is in electronic communication with the processor. The memory includes programming code for execution by the processor. The programming code is configured to spin the high-speed reagent bottle spinning device to spin the at least one reagent bottle to remove microparticles from a bottom surface of a septum of the at least one reagent bottle.

In another embodiment, another reagent manager for a diagnostic analyzer system is disclosed. The reagent manager includes a reagent manager housing, a high-speed reagent bottle spinning device, a processor, and a memory. The reagent manager housing houses reagent bottles. The high-speed reagent bottle spinning device is disposed within the reagent manager housing mated to at least one of the reagent bottles. The processor is in electronic communication with the high-speed reagent bottle spinning device. The memory is in electronic communication with the processor. The memory includes programming code for execution by the processor. The programming code is configured to spin the high-speed reagent bottle spinning device and the at least one mated reagent bottle forward and backward at a rate which removes microparticles from a bottom surface of a septum of the at least one mated reagent bottle. The programming code is configured to spin the high-speed reagent bottle spinning device so that: reagent disposed within the at least one mated reagent bottle moves forward at a speed forward rate of between 5,000 to 7,000 degrees per second, moves forward at an acceleration forward rate of between 110,000 degrees per second squared to 180,000 degrees per second squared, and moves forward at an angle of between 180 degrees to 360 degrees; the reagent within the at least one mated reagent bottle moves backward at a speed backward rate of between 5,000 to 7,000 degrees per second, moves backward at an acceleration backward rate of between 110,000 degrees per second squared to 180,000 degrees per second squared, and moves backward at an angle of between 180 degrees to 360 degrees; and there is a delay, after both the forward and the backward spinning of the at least one mated reagent bottle, in a range of between 250 milliseconds to 750 milliseconds.

In still another embodiment, a reagent manager of operating a reagent manager of a diagnostic analyzer is disclosed. In one step, a high-speed reagent bottle spinning device, disposed within a reagent manager housing of a reagent manager, is spun to remove microparticles from a bottom surface of a septum of a reagent bottle held within the reagent manager housing.

In yet another embodiment, a reagent manager of removing microparticles from a reagent storage container closure is disclosed. In one step, a reagent bottle is spun to force liquid within the reagent bottle to contact and remove microparticles from a bottom surface of a closure of a reagent bottle.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

FIG. 5 illustrates a cross-section view through line 5-5 of the embodiment of FIG. 4;

FIG. 6 illustrates a perspective view of one of the reagent bottles of the embodiment of FIG. 3 with the reagent cartridge having been detached from the reagent bottle and a cap of the reagent bottle also removed;

FIG. 7 illustrates a cross-section view through the reagent bottle of the embodiment of FIG. 6 with the cap reattached;

DETAILED DESCRIPTION

Figure 1:
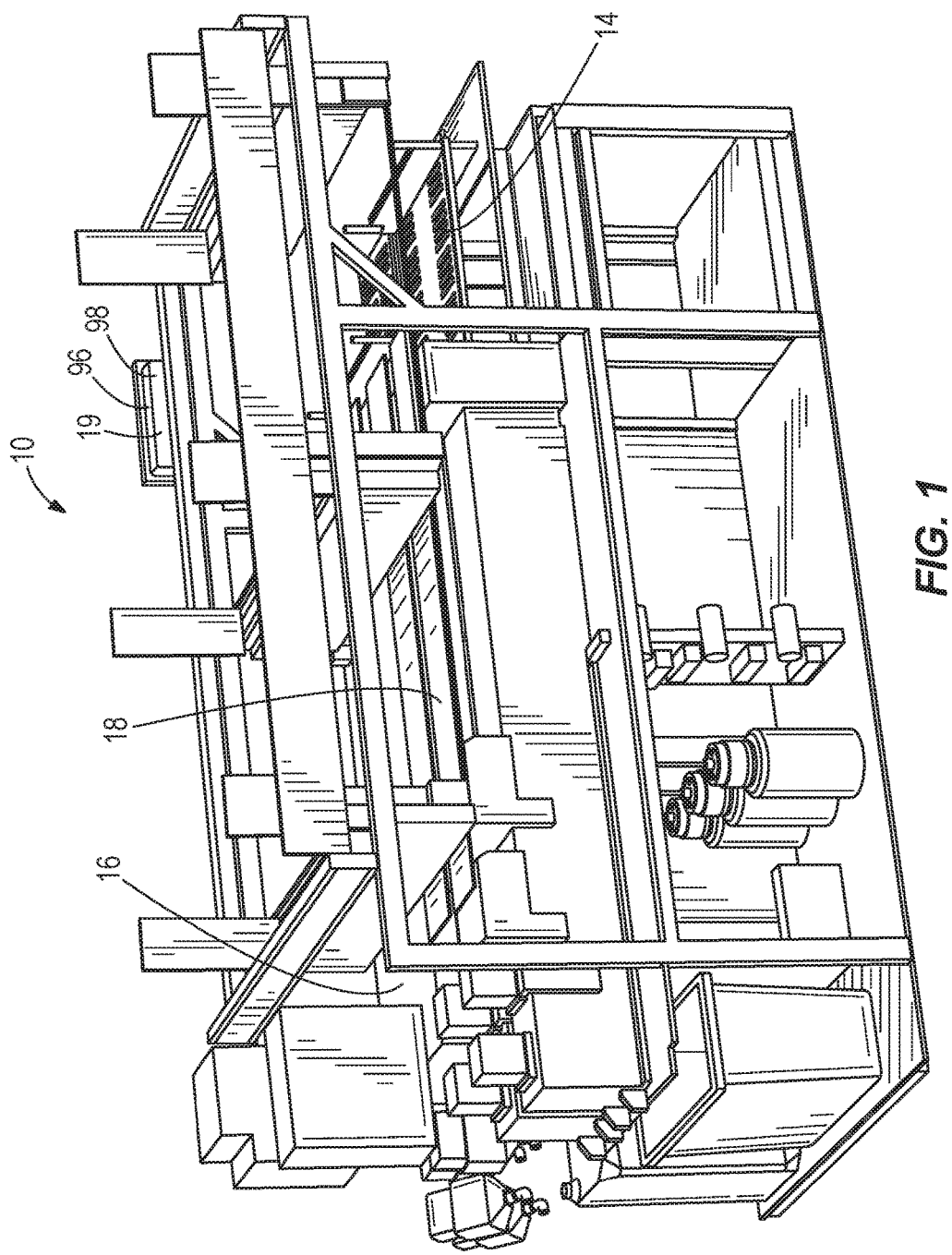
FIG. 1 illustrates a perspective view of one embodiment of a diagnostic analyzer system.
Figure 2:
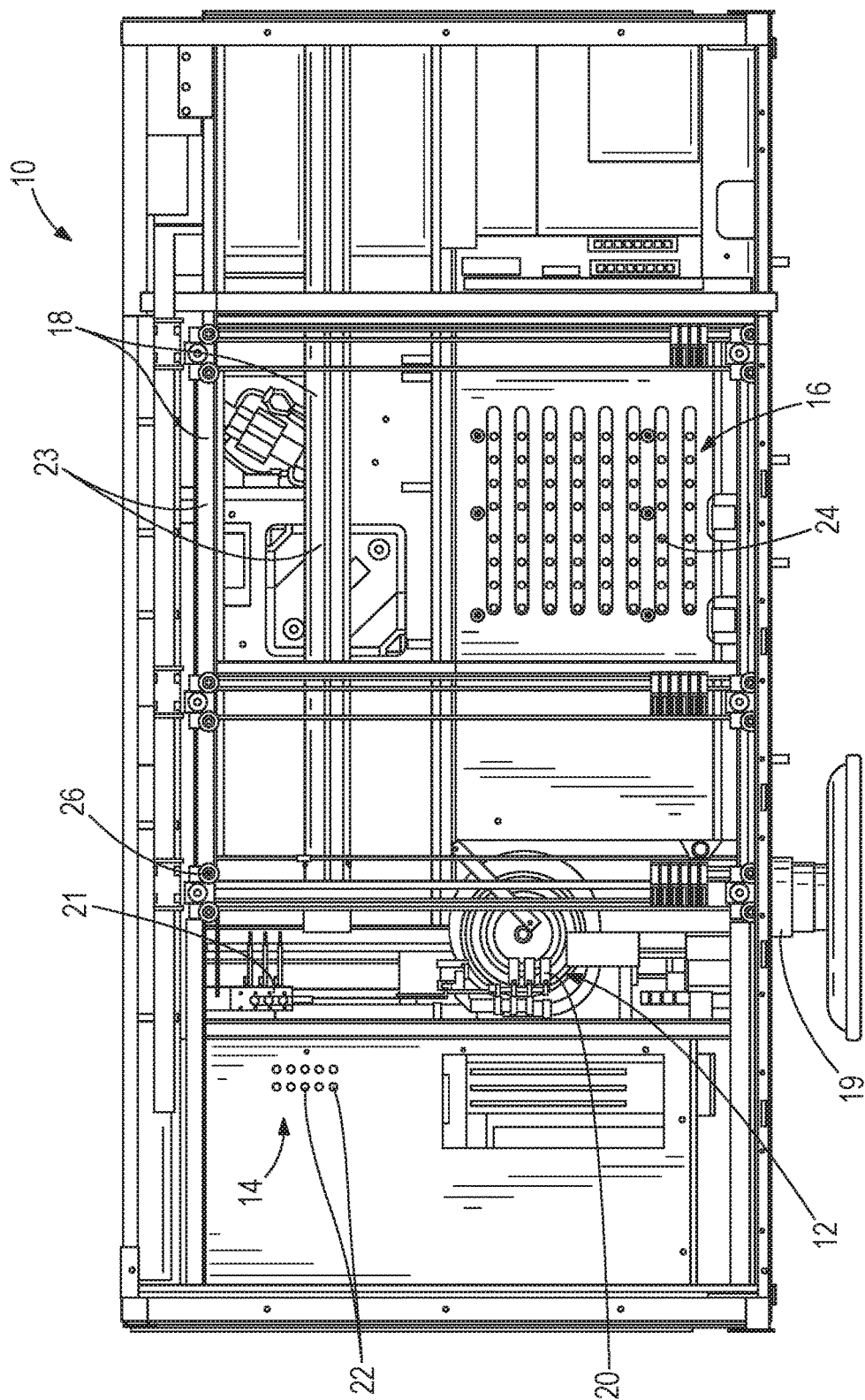
FIG. 2 illustrates a top view of the diagnostic analyzer system of the embodiment of FIG. 1.

FIGS. 1 and 2 respectively illustrate a perspective view and a top view of one embodiment of a diagnostic analyzer system 10. As shown collectively in FIGS. 1 and 2, the diagnostic analyzer system 10 comprises a reaction vessel loading zone 12, a sample storage zone 14, a reagent storage zone 16, a testing zone 18, and one or more processors 19. The one or more processors 19 may control the actions of the diagnostic analyzer system 10. The reaction vessel loading zone 12 comprises a zone which supplies reaction vessels 20 to the testing zone 18 preferably using a robot 21. The sample storage zone 14 comprises a zone which supplies samples 22 to the testing zone 18 for testing. The samples 22 comprise blood samples. The blood samples may be taken from a mammal, a human, an animal, or any type of living creature. The reagent storage zone 16 comprises a zone which supplies reagents 24 to the testing zone 18. The testing zone 18 comprises a zone which conducts testing on the samples 22 to determine a measurement, a property, a trait, or a condition of the samples 22. The testing zone 18 comprises two linear tracks 23. In other embodiments, the testing zone 18 may comprise any number of linear tracks 23. In still other embodiments, the testing zone 18 may comprise one or more moving tracks of varying configurations. The linear tracks 23 are made of stainless steel. The linear tracks 23 and the entire assemblies are conductive to eliminate a build-up of static electricity. The linear tracks 23 are identical. In other embodiments, the linear tracks 23 may vary. Motor 26 provides power for moving the linear tracks 23. In other embodiments, any number of motors 26 may be used to provide power for moving the linear tracks 23.

Figure 3:
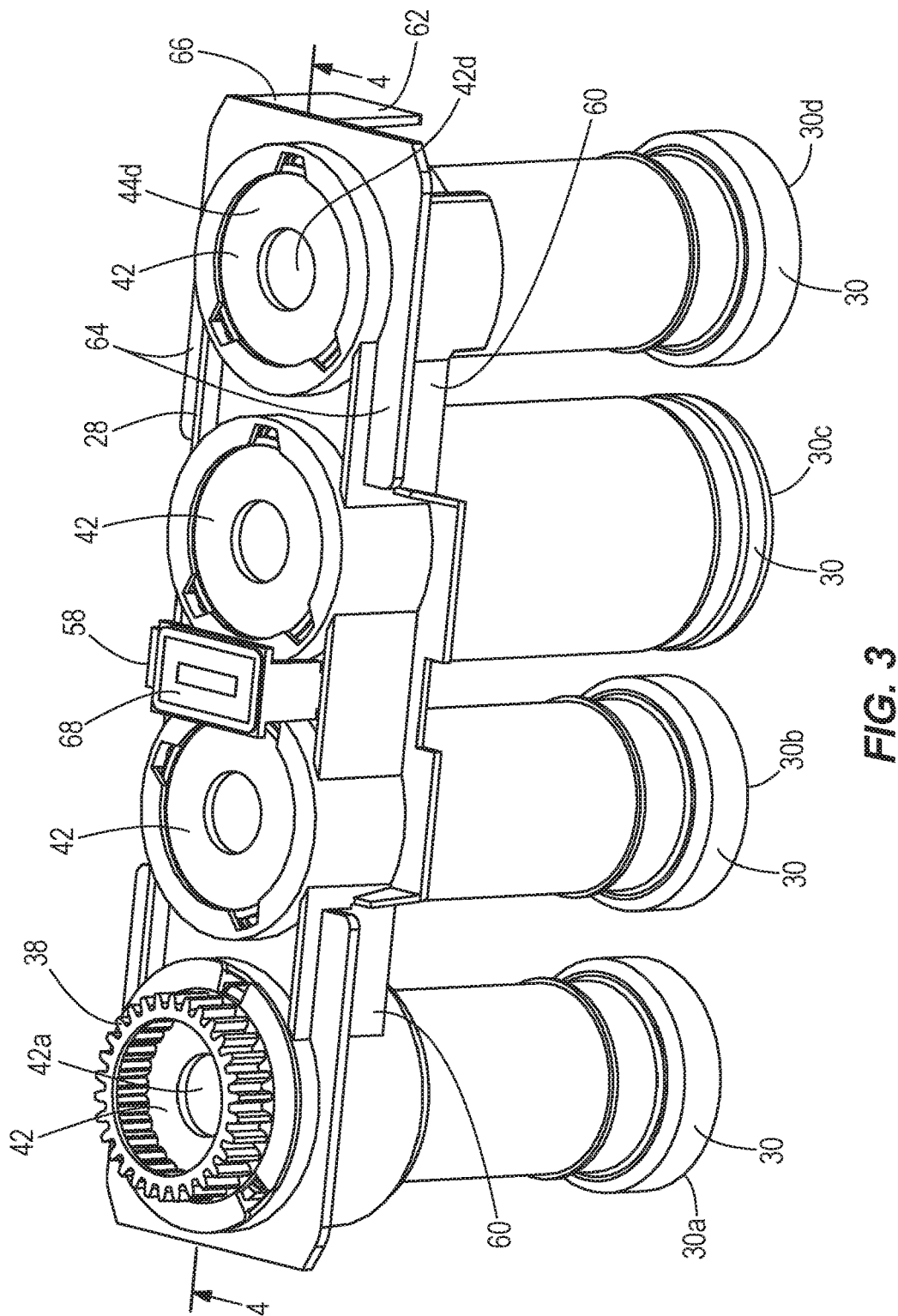
FIG. 3 illustrates a perspective view of one embodiment of a reagent cartridge attached to reagent bottles.
Figure 4:
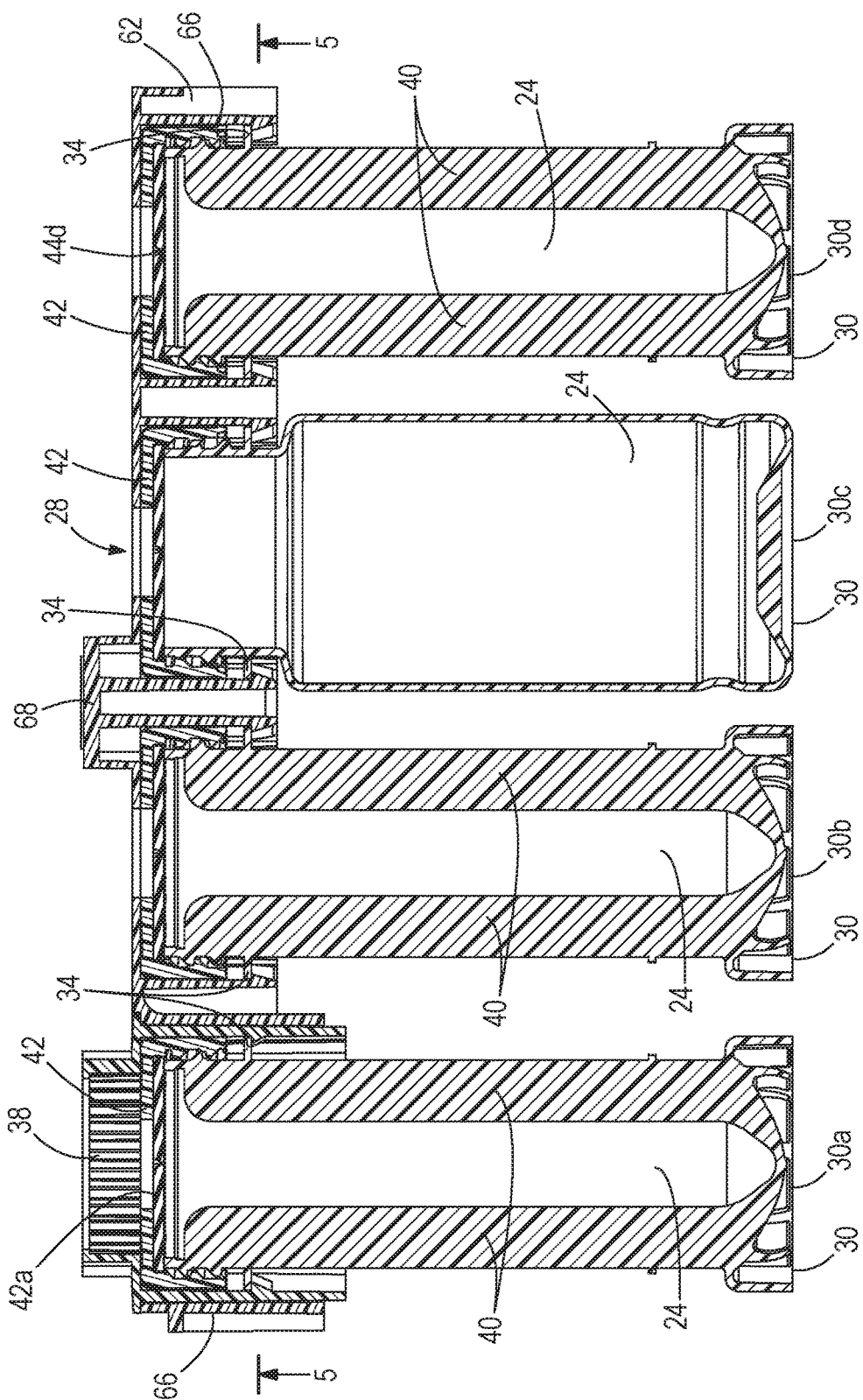
FIG. 4 illustrates a cross-section view through line 4-4 of the embodiment of FIG. 3.

FIG. 3 illustrates a perspective view of one embodiment of a reagent cartridge 28 attached to reagent bottles 30. FIG. 4 illustrates a cross-section view through line 4-4 of the embodiment of FIG. 3. FIG. 5 illustrates a cross-section view through line 5-5 of the embodiment of FIG. 4. As shown collectively in FIGS. 3-5, the reagent cartridge 28 comprises an injected molded part having snap members 32 which snap onto flanges 34 of the reagent bottles 30. The reagent bottles 30 comprise reagent bottles 30*a*, 30*b*, 30*c*, and 30*d* which each may contain varying types of reagent for running tests on samples being tested by the diagnostic analyzer system.

The reagent cartridge 28 and reagent bottles 30 contain common mating interfaces which allow the reagent cartridge 28 to attach/snap to differently sized reagent bottles 30 as long as the reagent bottles 30 contain the common mating interfaces. The common mating interfaces comprise circular walls 36 with the snap members 32 dispersed around the circular walls 36. This allows the reagent cartridge 28 to be attached to varying sized reagent bottles 30 containing varying amounts of reagent 24 (i.e. 30 ml injection molded bottles, 60 ml injection molded bottles, etc.). The reagent bottles 30 are assembled in the correct order at the time of manufacture. The reagent cartridge 28 holds the reagent bottles 30 in a tamper resistant manner as a result of the snap members 32. To remove the reagent bottles 30 from the reagent cartridge 28, a special tool or destructive means is required to avoid tampering.

The reagent cartridge 28 includes a dispersion gear 38 which snaps to reagent bottle 30*a* and which interfaces with a high-speed reagent bottle spinning device of a reagent manager (shown and discussed later) to provide, during a "cap-cleaning mode," for uniform dispersion of magnetic microparticles in bottle 30*a*. There are two internal fins 40 in each of reagent bottles 30*a*, 30*b*, and 30*d*. Reagent bottle 30*c* does not have internal fins. The two internal fins in reagent bottle 30*a* assist in dispersing the reagents 24 within the reagent bottle 30*a* by creating a turbulent flow when the dispersion gear 38 is spun by the high-speed reagent bottle spinning device or another spinning device of the reagent manager (shown and discussed later). In other embodiments, the reagent bottles 30*a*, 30*b*, and 30*d* may each have a varying number and size of fins 40. The spinning of the dispersion gear 38 by the high-speed bottle spinning device (shown and discussed later) in conjunction with the fins 40 within the reagent bottle 30a removes magnetic microparticles of the reagent 24 which may have accumulated/settled on an integrated septum 42a of bottle 30a during shipping (i.e. if the reagent cartridge 28 was upside down) by creating a turbulent flow of the reagent 24 towards and against the integrated septum 42a thereby removing the magnetic microparticles from the integrated septum 42a.

FIG. 6 illustrates a perspective view of one of the reagent bottles 30a of the embodiment of FIG. 3 with the reagent cartridge 28 having been detached from the reagent bottle 30a and a cap of the reagent bottle 30a also removed. FIG. 7 illustrates a cross-section view through the reagent bottle 30a of the embodiment of FIG. 6 with the cap 44 reattached. As shown collectively in FIGS. 6 and 7, the two fins 40 each extend internally from a bottom portion 46 of the reagent bottle 30a to adjacent a top portion 48 of the reagent bottle 30a. The length 50 of the two fins 40 is 84 mm long. In other embodiments, the length 50 may vary between 50 to 86 mm. The two fins 40 are disposed at an angle 52 of 90 degrees. In other embodiments, the angle 52 may vary. In still other embodiments, the number, size, configuration, and orientation of the fins 40 may further vary.

As shown collectively in FIGS. 3-5, the reagent bottles 30 held by the reagent cartridge 28 include integrated septum 42 which contain the reagents 24 in the reagent bottles 30 prior to use. These integrated septum 42 can be opened by a pipetting device (shown and discussed later) of the diagnostic analyzer system without human intervention. The septum 42 are made of thermoplastic polymer and are each molded to have six, co-centered, and interconnected serrated slots 54 forming six leafs 56. The serrated slots 54 are designed to stay intact (unbroken) during manufacture, storage and shipment, but open in a predictable manner when the pipetting device (shown and discussed later) of the diagnostic analyzer system penetrates them. The integrated septum 42 control evaporation of the reagents 24 for up to 30 days or 500 uses, whichever comes first. The leafs 56, defined by the serrated slots 54, open during pipetting and then spring back to close or minimize the reagent bottle openings to control the evaporation rate of the reagents 24.

The reagent cartridge 28 includes a spring member 58 which is configured to interface with a "pick and place" robot (shown and discussed later) of the diagnostic analyzer system so that the reagent cartridge workflow can be automated by the robot depressing and releasing the spring member 58 so that the reagent cartridge 28 can be lifted and moved. The design/shape of the surfaces 60 of the reagent cartridge 28 allow the robot to "pick and place" the reagent cartridge 28. As discussed later, this includes loading the reagent cartridge 28 into a storage area of the diagnostic analyzer system, reading a barcode 62 of the reagent cartridge 28, placing the reagent cartridge 28 in an operating area of the diagnostic analyzer system for pipetting the reagent 24 out of the reagent bottles 30, and disposing of the reagent cartridge 28 and the attached reagent bottles 30 when the reagent bottles 30 are empty. The spring member 58 interfaces with the diagnostic analyzer system to ensure accurate positioning of the septum 42 relative to the pipetting device of the diagnostic analyzer system to ensure proper operation.

To ensure accurate positioning of the septum 42 relative to the pipetting device, rail members 64 of the reagent cartridge 28 slide into mating guides (shown and discussed later) of the diagnostic analyzer system. When the spring member 58 reaches the correct position within the diagnostic analyzer system, due to the rail members 64 of the reagent cartridge 28 sliding along the mating guides of the diagnostic analyzer system, the spring member 58 snaps into a pocket (shown and discussed later) of the diagnostic analyzer system to lock the reagent cartridge 28 into the correct spot relative to the pipetting device. To prevent a user from placing the reagent cartridge 28 into the diagnostic analyzer system in an incorrect orientation, keying surfaces 66 are provided on the reagent cartridge 28 which interact with a corresponding surface (shown and discussed later) of the diagnostic analyzer system that will not allow the reagent cartridge 28 to be installed in an incorrect orientation.

The reagent cartridge 28 includes a Radio-Frequency-Identification (RFID) device (or tag) 68 which is mounted on the reagent cartridge 28 to provide for storage of data in a read/write format (in a nonvolatile read/write memory) so that identification and inventory of the reagent 24 can be automated and time-efficient. The RFID device 68 stores reagent cartridge history to prevent running the "cap cleaning mode" on a previously opened cartridge 28 (i.e. when the septum has been punctured by the pipetting device). Analyzer software will update the status of the history by reading and writing to the RFID device 68. The RFID device 68 also assists in determining the position of the reagent cartridge 28 in any of the storage area within the reagent storage subsystem of the diagnostic analyzer system. As shown and discussed more thoroughly later, the diagnostic analyzer system reads each position of the reagent cartridges 28 within the diagnostic analyzer system, one at a time, using a multiplexed array of antenna positioned within the diagnostic analyzer system above the cartridge 28 positions. If a reagent cartridge 28 is present, the RFID device 68 will respond. High frequency RFID devices 68 are used so that only reagent cartridges 28 in proximity to antenna will respond.

As a back-up to the RFID device 68, the reagent cartridge 28 also contains a barcode 62 which allows the diagnostic analyzer system to obtain information regarding the reagent bottles 30 even if the RFID device 68 is not working. The information may comprise any type of pertinent information regarding the reagent bottles 30 at the time of factory filling such as the type of reagent 24 they each hold, or other information.

To avoid exposure of light to reagent bottle 30d, the reagent cartridge 28 is attached to a colored (opaque) reagent bottle 30d, a colored cap 44d, a colored septum 42d, and a dustcover (not shown), which snaps onto the reagent cartridge 28, to limit the exposure of the reagent 24 in reagent bottle 30d. In other embodiments, these features may be used in any of the other reagent bottles 30a, 30b, or 30c to avoid exposure to light.

The reagent cartridge 28, in combination with the diagnostic analyzer system as discussed more thoroughly subsequently, relieve a user from performing the tedious operations of inverting reagent bottles 30 for cap cleaning after shipment, of installing septum 42 into the reagent bottles 30, of installing the reagent bottles 30 into the diagnostic analyzer system in the correct position, and of removing the reagent bottles 30 from the diagnostic analyzer system. It also adds modes of controls to prevent open reagent bottles 30 from being run through the cap cleaning mode, fast onboard inventory, and tamper resistance to maintain the integrity of the reagents 24. The reagent cartridge 10, in combination with the diagnostic analyzer system as discussed more thoroughly subsequently, can reduce the hands-on time for an operator to load reagents 24 from forty minutes to under two minutes. This is a large competitive advantage over current designs.

Figure 8:
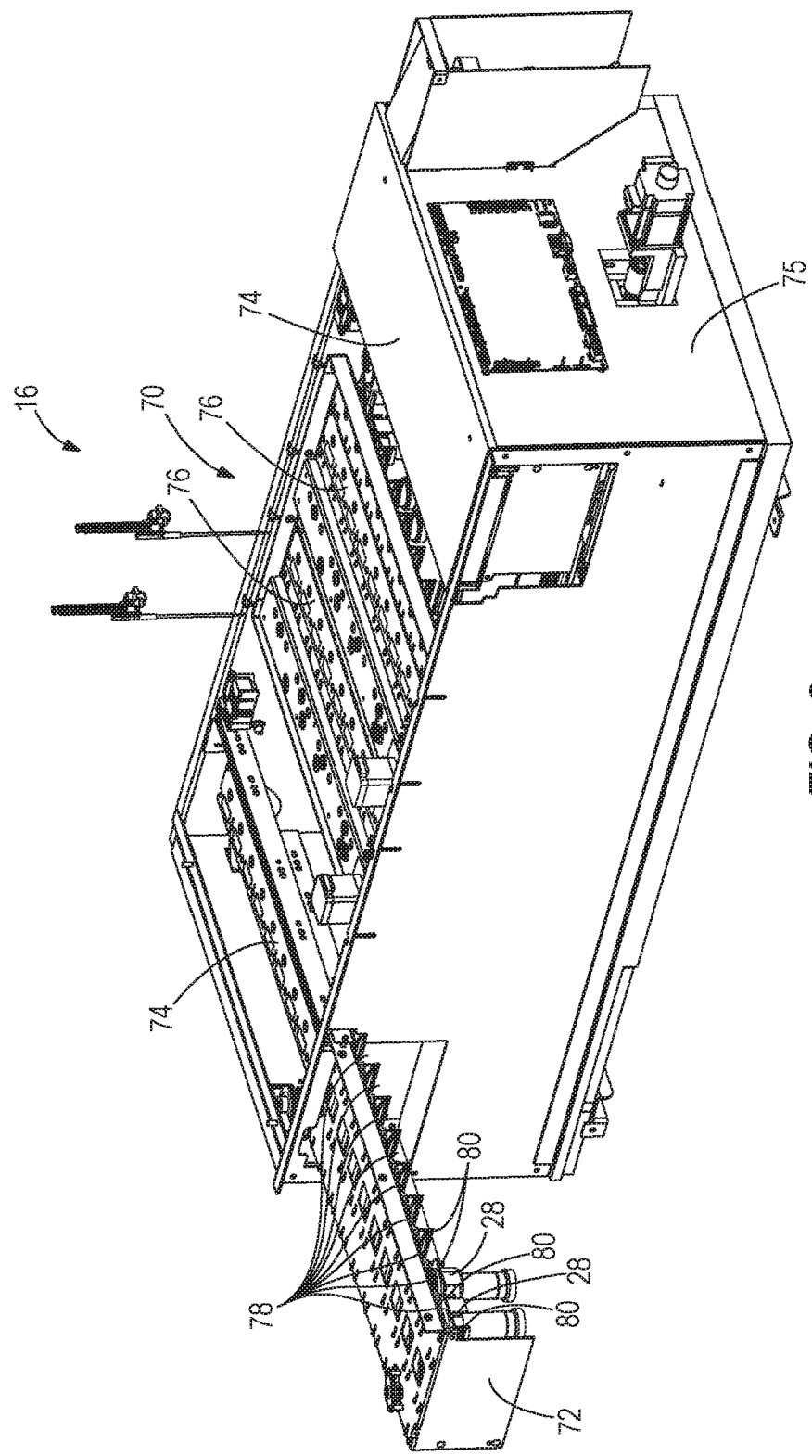
FIG. 8 illustrates a perspective view of one embodiment of a reagent manager, with a storage drawer of a storage area of the reagent manager open, which may be utilized in a reagent storage zone of the diagnostic analyzer system of FIG. 1.
Figure 9:
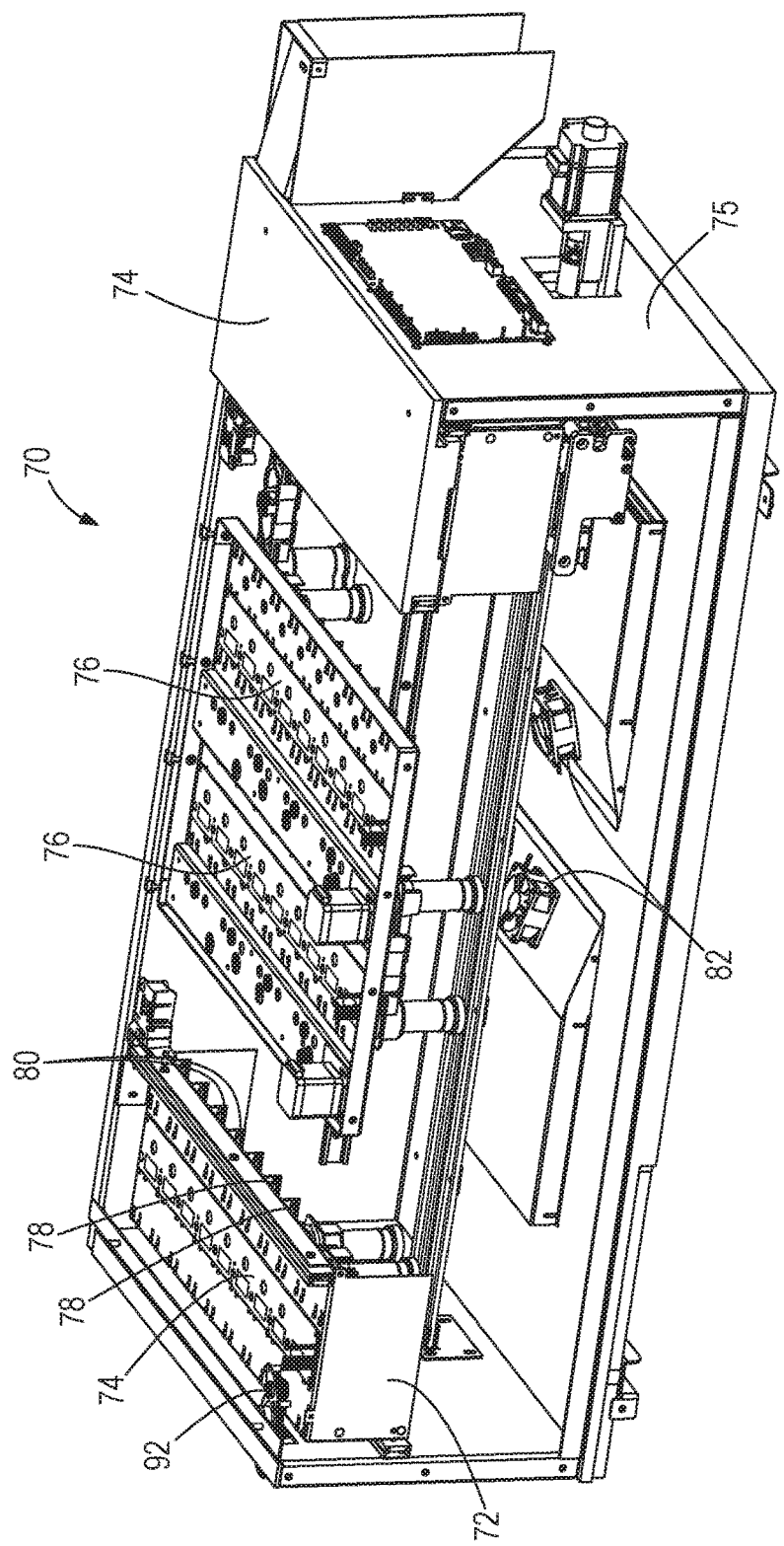
FIG. 9 illustrates a perspective view of the reagent manager of the embodiment of FIG. 8 with the storage drawer closed and a front wall removed.

FIG. 8 illustrates a perspective view of one embodiment of a reagent manager 70, with a storage drawer 72 of a storage area 74 of the reagent manager 70 open, which may be utilized in a reagent storage zone 16 of the diagnostic analyzer system 10 of FIG. 1. FIG. 9 illustrates a perspective view of the reagent manager 70 of the embodiment of FIG. 8 with the storage drawer 72 closed and a front wall removed. The reagent manager 70 contains a reagent manager housing 75 which houses two storage areas 74 and two operating areas 76. Each storage area 74 comprises a storage drawer 72 which is configured to move from the open position shown in FIG. 8 to the closed position shown in FIG. 9.

Figure 10:
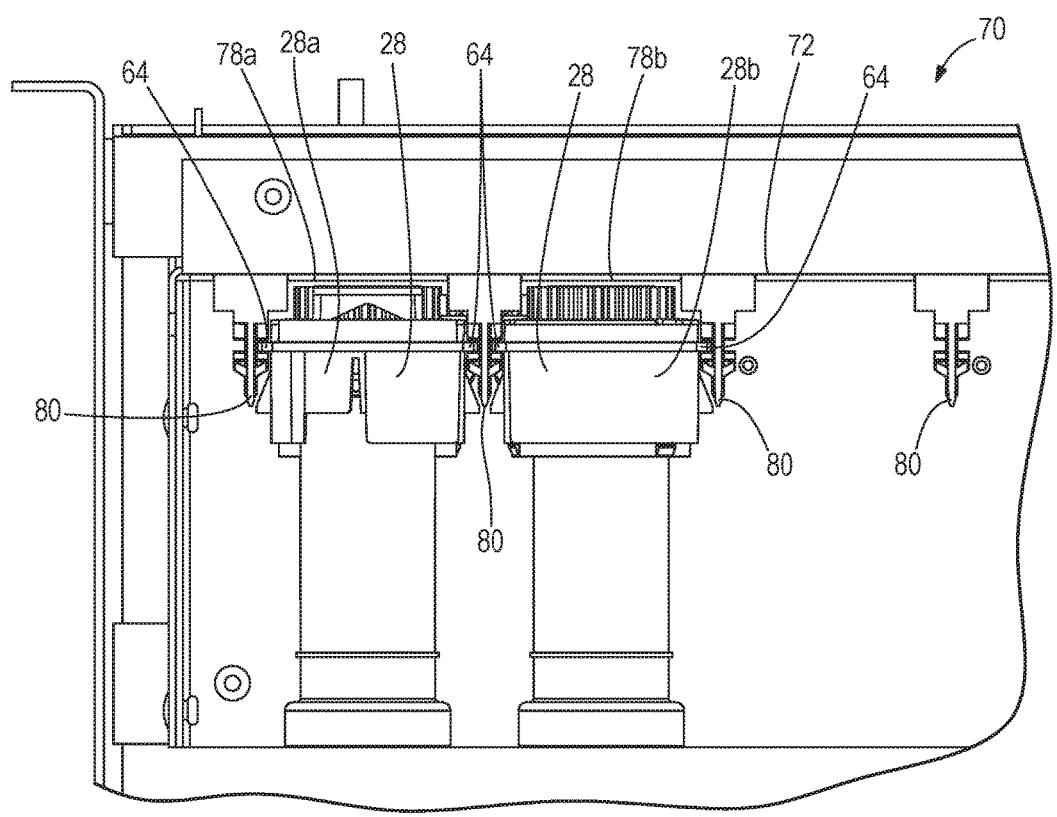
FIG. 10 illustrates a side-view of a portion of the storage drawer of the reagent manager of the embodiment of FIG. 9 with two reagent cartridges inserted into two of the rows of the storage drawer.

Each storage drawer 72 comprises nine rows 78 into which eight separate reagent cartridges 28 can be inserted into in parallel alignment when the storage drawer 72 is open. The ninth row is reserved for barcode scanning. As shown in FIG. 10, the rail members 64 of each reagent cartridge 28 slide into and along parallel and opposed mating guide members 80 of each row 78 in order to support the reagent cartridges 28 in the rows 78 of the storage drawer 72. The structure of the reagent cartridges 28 ensures that they are inserted into the rows 78 of the storage drawer 72 correctly. After the reagent cartridges 28 are inserted into the rows 78 of the storage drawer 72, the storage drawer 72 is closed as shown in FIG. 9. In other embodiments, the storage areas 74, the rows 78 in each storage drawer 72 of each storage area 74, and the operating areas 76 may vary in number, configuration, or in other ways. Cooling devices 82 are disposed below the storage areas 74 and the operating areas 76 for keeping the reagent manager refrigerated. The cooling devices 82 may comprise two peltier coolers to keep the inside temperature of the reagent manager 70 at two to twelve degrees Celsius.

The storage drawers 72 may be opened and closed in order to insert more reagent cartridges 28 into the reagent manager 70 without disrupting the continuous processing of the reagent cartridges 28 in the operating areas 76 during testing of samples. Moreover, a user may load the storage drawers 72 with reagent cartridges 28 in any random order and a robot (shown and discussed later) of the reagent manager 70 will redistribute the reagent cartridges 28 within the reagent manger 70 in the appropriate order for testing.

Figure 11:
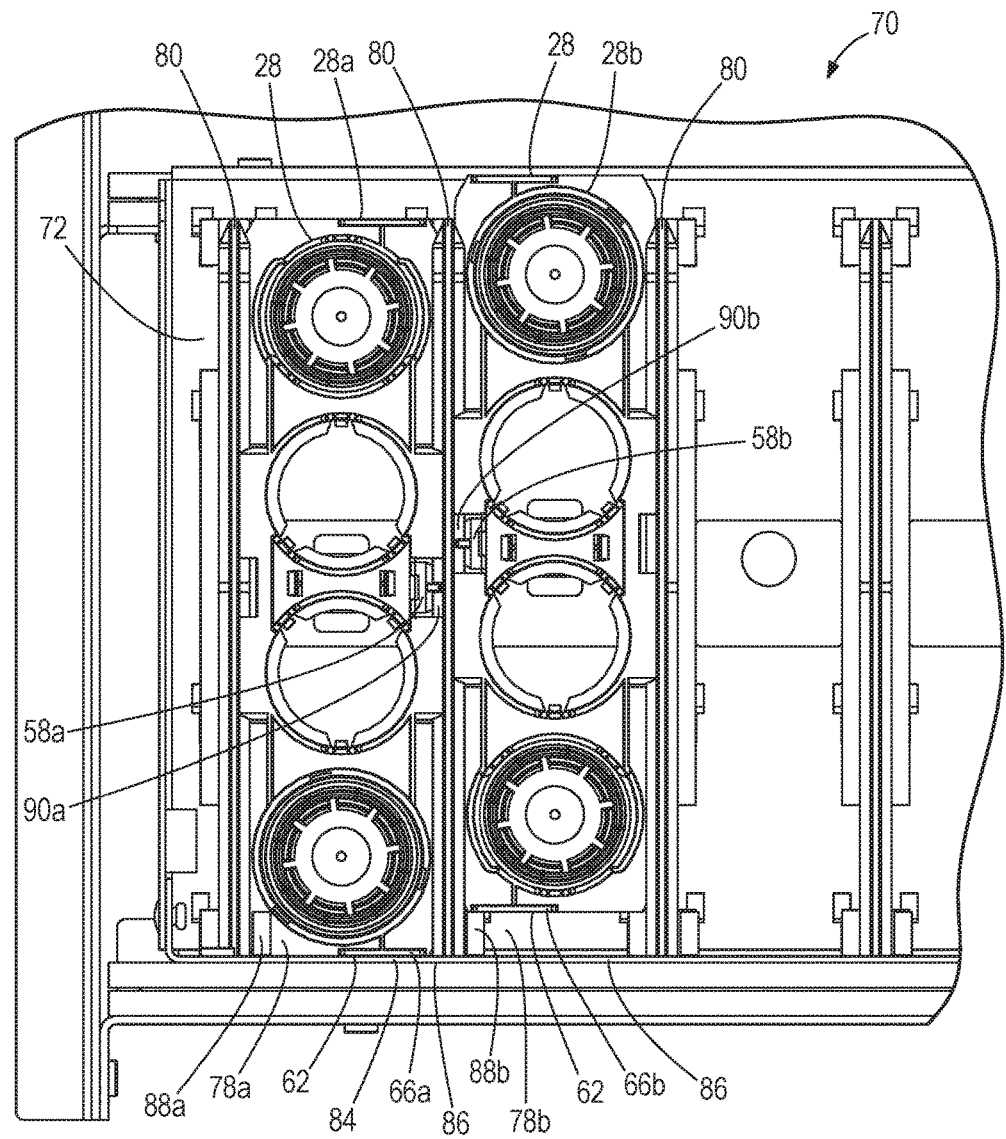
FIG. 11 illustrates bottom view of the portion of the storage drawer of the reagent manager of the embodiment of FIG. 10 with the two reagent cartridges inserted into the two rows of the storage drawer.

FIG. 10 illustrates a side-view of a portion of the storage drawer 72 of the reagent manager 70 of the embodiment of FIG. 9 with two reagent cartridges 28 inserted into two of the rows 78 of the storage drawer 72. FIG. 11 illustrates a bottom view of the portion of the storage drawer 72 of the reagent manager 70 of the embodiment of FIG. 10 with the two reagent cartridges 28 inserted into the two rows 78 of the storage drawer 72. As shown collectively in FIGS. 10-11, reagent cartridge 28a has been inserted correctly into row 78a, but reagent cartridge 28b has been inserted incorrectly into row 78b (i.e. the other way around).

The keying surface 66a of reagent cartridge 28a is disposed flush against the side 84 of the storage drawer 72 allowing the barcode reader 86 to read the barcode 62. The alignment surface 88a of the storage drawer 72 does not interfere with the keying surface 66a of reagent cartridge 28a because it was correctly inserted within row 78a. The spring member 58a of reagent cartridge 28a has snapped into place within pocket 90a of one of the opposed mating guide members 80 once the reagent cartridge 28a reached the correct position thereby securing the reagent cartridge 28a in the correct position within row 78a.

However, the alignment surface 88b of the storage drawer 72 is interfering with the keying surface 66b of reagent cartridge 28b because it was incorrectly inserted within row 78b. This has resulted in reagent cartridge 28b sticking out of row 78b because the alignment surface 88b is contacting the keying surface 66b thereby preventing the keying surface 66b from being disposed flush against the side 84 of the storage drawer 72. As a result, the user is alerted that reagent cartridge 28b needs to be turned around and reinserted into row 78b of the storage drawer 72 because the storage drawer 72 won't completely close back into the reagent manager 70. It is further noted that the spring member 58b of reagent cartridge 28b has not snapped into place within the pocket 90b of one of the opposed mating guide members 80 because the reagent cartridge 28b is disposed in an incorrect position within row 78b.

Once the user removes the reagent cartridge 28b from row 78b and inserts the reagent cartridge 28b the correct way into row 78b the keying surface 66b will be disposed flush against the side 84 of the storage drawer 72 allowing the barcode reader 86 to read the barcode 62 of the reagent cartridge 28b. In this correct position, the spring member 58b of reagent cartridge 28b will snap into place within the pocket 90b of one of the opposed mating guide members 80 thereby locking the reagent cartridge 28b in the correct position within row 78b.

Figure 12:
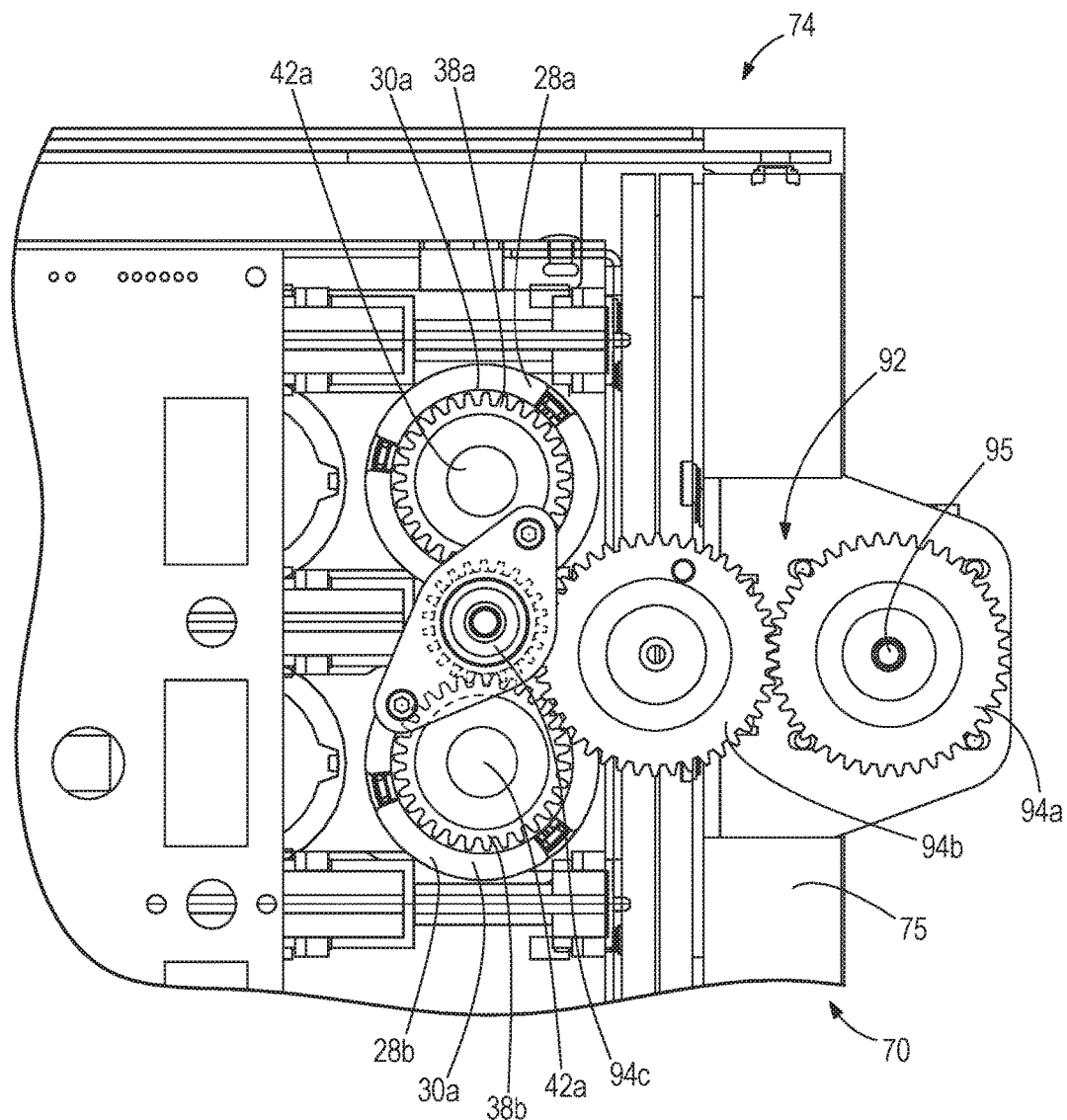
FIG. 12 illustrates a close-up view of a high-speed reagent bottle spinning device within the storage area of the reagent manager housing of the reagent manager of the embodiment of FIG. 9 in contact with dispersion gears of two reagent cartridges.

FIG. 12 illustrates a close-up view of a high-speed reagent bottle spinning device 92 within the storage area 74 of the reagent manager housing 75 of the reagent manager 70 of the embodiment of FIG. 9 in contact with dispersion gears 38a and 38b of two reagent cartridges 28a and 28b. The high-speed reagent bottle spinning device 92 comprises a gear-chain plurality of gears 94a, 94b, and 94c. Motor 95 rotates gear 94a. Gear 94a rotates gear 94b. Gear 94b rotates gear 94c. Gear 94c rotates dispersion gears 38a and 38b of reagent cartridges 28a and 28b. The processor 19 of FIG. 1 is in electronic communication with the high-speed reagent bottle spinning device 92 and controls its actions. As shown in FIG. 1, the processor 19 contains and/or is in electronic communication with a memory 96 containing programming code 98 for execution by the processor 19.

The programming code 98 of FIG. 1 is configured to spin the high-speed reagent bottle spinning device 92 of FIG. 12 to spin the dispersion gears 38a and 38b of reagent cartridges 28a and 28b which in turn spin the attached reagent bottles 30a of the reagent cartridges 28a and 28b (see also FIGS. 3-5) to remove microparticles from the bottom surface of the septum 42a of each of the reagent bottles 30a during a cap-cleaning mode. The spinning of the dispersion gears 38a and 38b by the high-speed bottle spinning device 92 in conjunction with the two fins 40 (see FIGS. 4, 6, and 7 and the parameters of the fins 40 discussed previously) within the reagent bottles 30a creates a turbulent flow of the reagent 24 towards and against the septum 42a of each of the reagent bottles 30a thereby removing magnetic microparticles which may have accumulated/settled on the integrated septum 42a of the reagent bottles 30a during shipping (i.e. if the bottles 30a were upside down) by splashing the reagent 24 onto the integrated septum 42a to remove the microparticles.

The programming code 98 is configured to spin the high-speed reagent bottle spinning device 92 forward and backward at a rate which removes the microparticles from the bottom surfaces of the septum 42a of the reagent bottles 30a. For purposes of this disclosure the term 'cycle' is defined as each time the high-speed reagent bottle spinning device 92 goes in one direction. For instance, if the high-speed reagent bottle spinning device 92 first goes in a forward direction and then goes in a backward direction this movement would comprise two cycles with each of the forward movement and the backward movement comprising a separate cycle. The programming code 98 is configured to spin the high-speed reagent bottle spinning device 92, and correspondingly the reagent bottles 30a, in a range of 40 to 80 forward and backward cycles for a total time in a range of 27 seconds to 55 seconds. It should be noted that each cycle is ideally in a range of 40 milliseconds to 50 milliseconds with a delay in-between each cycle of 250 milliseconds to 750 milliseconds, and ideally a delay of 500 milliseconds. In a preferred embodiment, the programming code 98 is configured to spin the high-speed reagent bottle spinning device, and correspondingly the reagent bottles 30a, for a total of 60 forward and backward cycles for a total time of 35 to 45 seconds including the delays.

The programming code 98 is configured to spin the high-speed reagent bottle spinning device 92 forward so that the reagent 24 disposed within the reagent bottles 30a moves forward at a speed forward rate of between 5,000 to 7,000 degrees per second, moves forward at an acceleration forward rate of between 110,000 degrees per second squared to 180,000 degrees per second squared, and moves forward at an angle of between 180 degrees to 360 degrees. In a preferred embodiment, the programming code 98 is configured to spin the high-speed reagent bottle spinning device 92 forward so that the reagent 24 disposed within the reagent bottles 30a moves forward at a speed forward rate of 5,625 degrees per second, moves forward at an acceleration forward rate of 135,000 degrees per second squared, and moves forward at an angle of 281 degrees.

The programming code 98 is configured to spin the high-speed reagent bottle spinning device 92 backward so that the reagent 24 disposed within the reagent bottles 30a moves backward at a speed backward rate of between 5,000 to 7,000 degrees per second, moves backward at an acceleration backward rate of between 110,000 degrees per second squared to 180,000 degrees per second squared, and moves backward at an angle of between 180 degrees to 360 degrees. In a preferred embodiment, the programming code 98 is configured to spin the high-speed reagent bottle spinning device 92 backward so that the reagent 24 disposed within the reagent bottles 30a moves backward at a speed backward rate of 5,625 degrees per second, moves backward at an acceleration backward rate of 135,000 degrees per second squared, and moves backward at an angle of 281 degrees.

If the particular reagent 24 requires an anti-foaming (or bubble-popping) process, the programming code 98 is configured to spin the high-speed reagent bottle spinning device 92 in between each cycle a predetermined number of one-directional anti-foam movements to de-foam (or bubble-pop) the reagent 24 within the reagent bottle 30a. In one embodiment, if the particular reagent 24 requires an anti-foaming process, the programming code 98 is configured to spin the high-speed reagent bottle spinning device 92 a total of 30 high-speed backward and forward cycles (with a backward and forward movement being defined as 2 cycles) with the same speed, acceleration, delay, and angle parameters previously discussed. In between each of the first 6 cycles (i.e. forward, backward, forward, backward, forward), the programming code 98 is configured to spin the high-speed reagent bottle 92 in a total of 3 one-directional anti-foam movements to de-foam the reagent 24.

Figure 13:
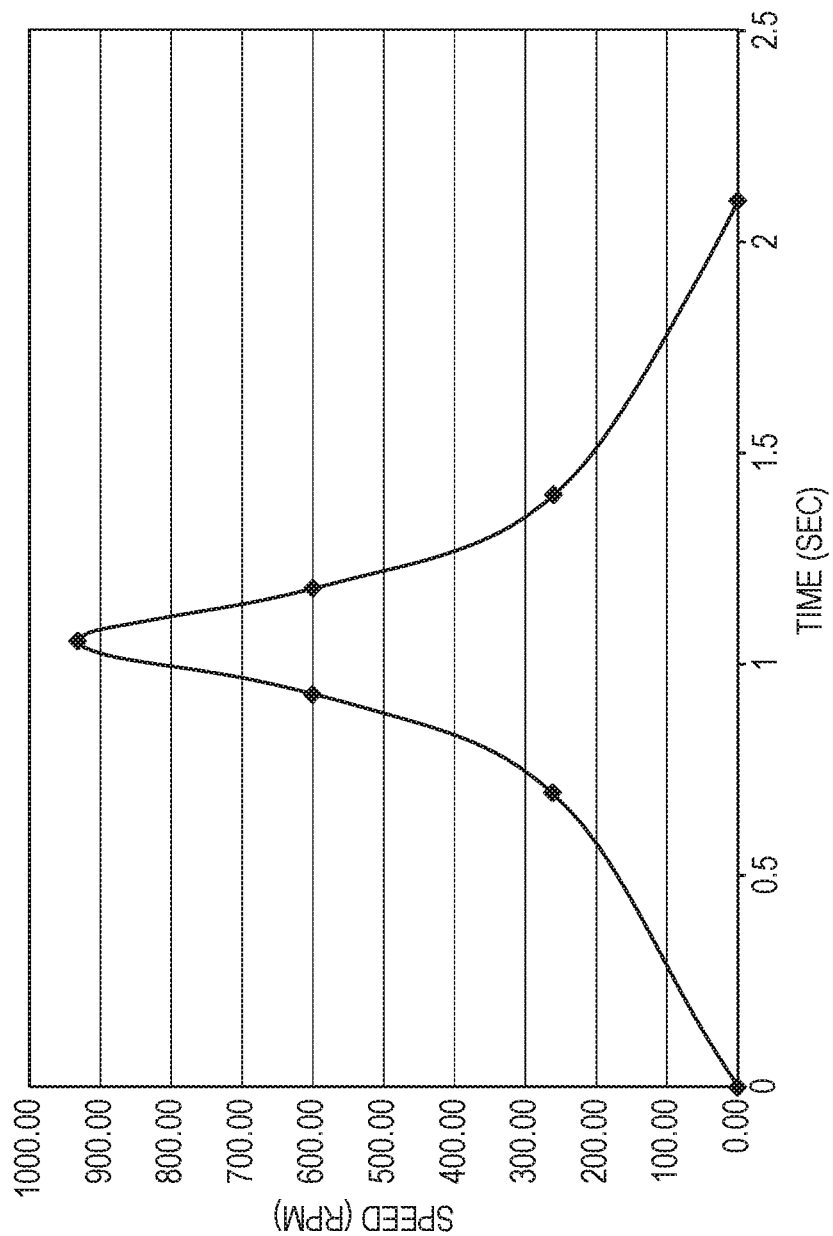
FIG. 13 illustrates one embodiment of a graph which may be used for one-directional anti-foam movements to de-foam reagent with speed being plotted on the Y-axis and time being plotted on the X-axis.

FIG. 13 illustrates one embodiment of a graph which may be used for each of the one-directional anti-foam movements to de-foam the reagent with speed being plotted on the Y-axis and time being plotted on the X-axis. As shown, each anti-foam movement of the high-speed reagent bottle spinning device 92 may last 2.1 seconds in one direction accelerating between 0 to 1.05 seconds and decelerating between 1.05 to 2.1 seconds. For instance, after the first high-speed cycle in the forward direction and the subsequent delay, the high-speed reagent bottle spinning device 92 may spin forward in three consecutive one-directional anti-foam movements all in the forward direction and all having the parameters as shown in FIG. 13. After the second high-speed cycle in the backward direction and the subsequent delay, the high-speed reagent bottle spinning device 92 may spin backward in three consecutive one-directional anti-foam movements all in the backward direction and all having the parameters as shown in FIG. 13. This process may continue for each of the next 4 high-speed cycles through the $6^{th}$ total high-speed cycle.

After the 6th total high-speed cycle, in between each of high-speed cycles 6 through 12, the programming code 98 is configured to spin the high-speed reagent bottle 92 in a total of 5 one-directional anti-foam movements (having the parameters of FIG. 13) to de-foam the reagent 24. After the 12th total high-speed cycle, in between each of high-speed cycles 12 through 18, the programming code 98 is configured to spin the high-speed reagent bottle 92 in a total of 7 one-directional anti-foam movements (having the parameters of FIG. 13) to de-foam the reagent 24. After the $18^{th}$ total high-speed cycle, in between each of high-speed cycles 18 through 30, the programming code 98 is configured to spin the high-speed reagent bottle 92 in a total of 9 one-directional anti-foam movements (having the parameters of FIG. 13) to de-foam the reagent 24. The delay in between each high-speed spin cycle and each antifoam one-directional movement may comprise 500 milliseconds. The total time to complete the entire 30 cycle high-speed spin and anti-foam process may be done in a range of 6 to 8 minutes.

In such manner, the high-speed reagent bottle spinning device 92 may be used to both remove reagent 24 from the bottom surfaces of the septum 42a of the reagent bottles 30a and to de-foam (bubble pop) the reagent 24 within the reagent bottles 30a. In other embodiments, the high-speed reagent bottle spinning device 92 may utilize different numbers, durations, speeds, accelerations, delay, angle, or other parameter high-speed spin or de-foam (bubble pop) movements to remove the reagent 24 from the bottom surfaces of the septum 42a of the reagent bottles 30a and to de-foam the reagent 24 within the reagent bottles 30a.

Figure 14:
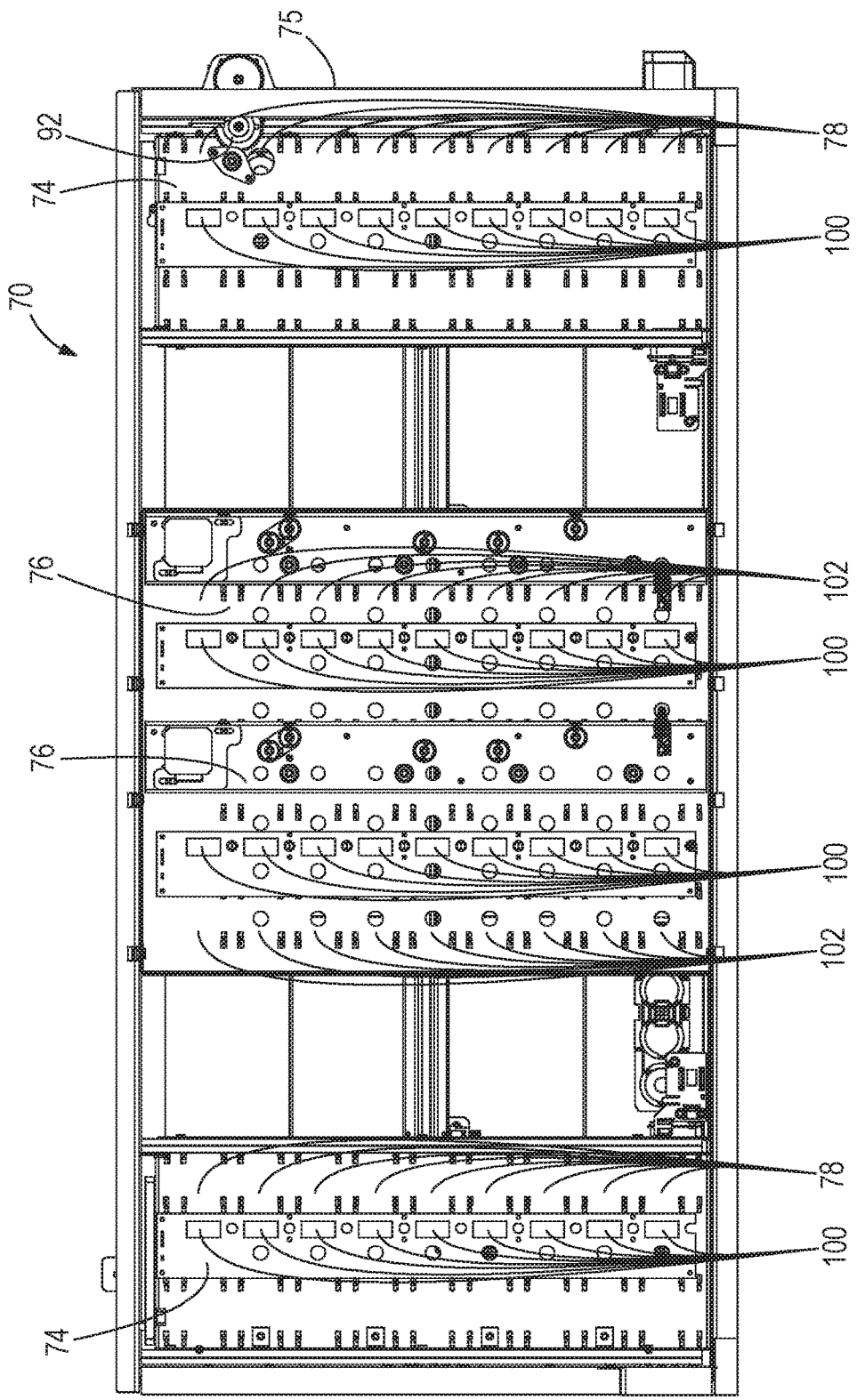
FIG. 14 illustrates a top view of the of the reagent manager of the embodiment of FIG. 9 with the outer surface of the reagent manager housing completely removed to expose antennas disposed throughout.
Figure 15:
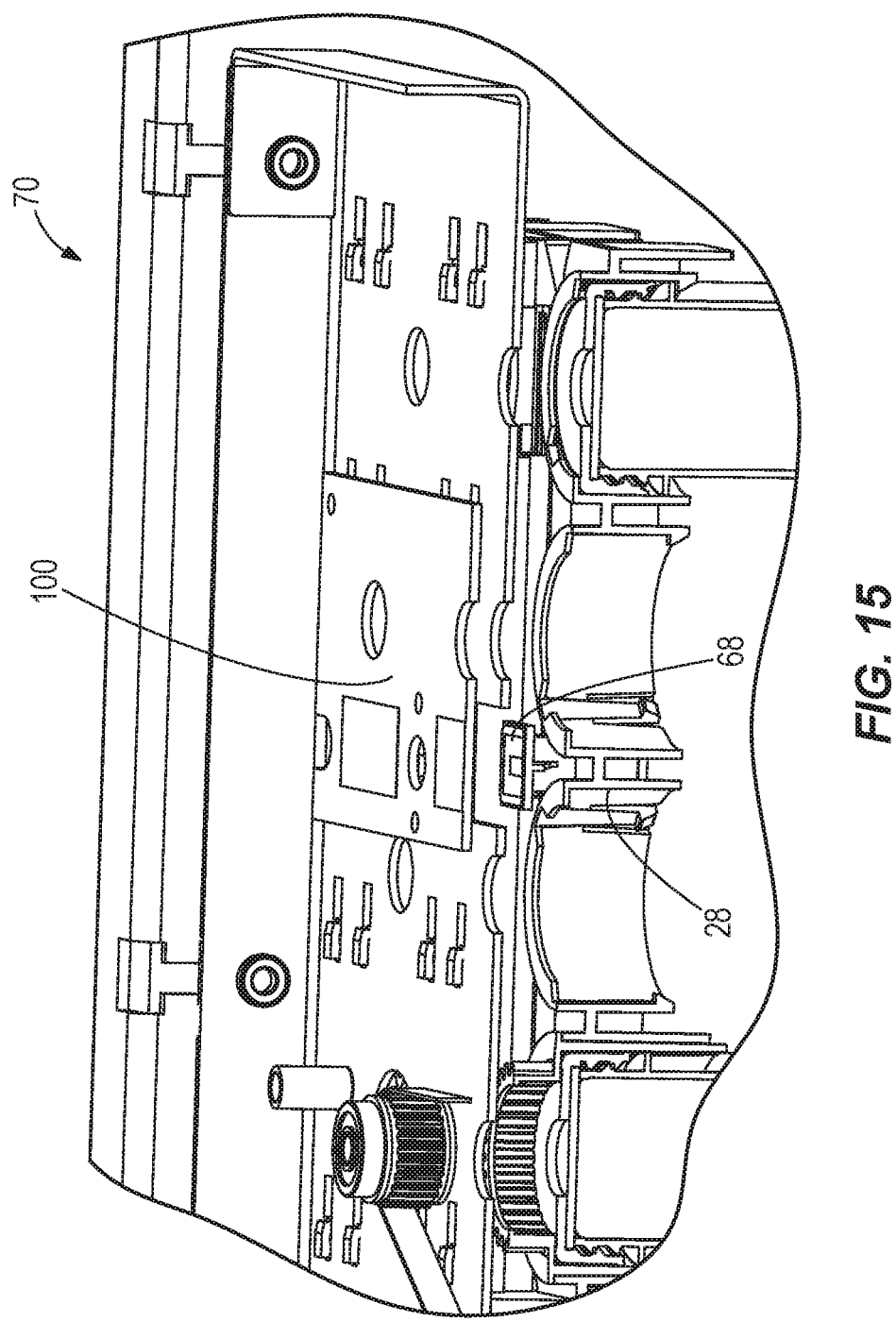
FIG. 15 illustrates a cross-section view through a portion of the reagent manager of the embodiment of FIG. 14 to show how the antennas of the reagent manager read and write-to the RFID devices of the reagent cartridges.

FIG. 14 illustrates a top view of the of the reagent manager 70 of the embodiment of FIG. 9 with the outer surface of the reagent manager housing 75 completely removed to expose antennas 100 disposed throughout. FIG. 15 illustrates a cross-section view through a portion of the reagent manager 70 of the embodiment of FIG. 14 to show how the antennas 100 of the reagent manager 70 read and write-to the RFID devices 68 of the reagent cartridges 28. As shown in FIG. 14, there are a total of thirty-six antennas 100 spread throughout the ceiling of the storage areas 74 and operating areas 76 of the reagent manager 70. In particular, one antenna 100 is disposed in each of the nine rows 78 of each of the two storage areas 74 for a total of eighteen antennas 100 spread throughout the two storage areas 74. Similarly, one antenna 100 is disposed in each of the nine rows 102 of each of the two operating areas 76 for a total of eighteen antennas 100 spread throughout the two operating areas 76.

The antennas 100 are in electronic communication with the processor 19 of FIG. 1 in order to determine the precise locations, identities, and other information regarding the reagent cartridges 28 within the storage areas 74 and operating areas 76 of the reagent manager 70 by communicating with the RFID devices 68 of the reagent cartridges 28. The antennas 100 are configured to read the information from or write the information to the RFID devices 68 of the reagent cartridges 28 as shown in FIG. 15. The information may comprise information such as test volume, number of days onboard, instrument identification on which the reagent cartridge 28 was used, level of liquid in each of the reagent bottles 30, or other pertinent information. The information may include an indicator as to whether the high-speed reagent bottle spinning device 92 has removed the microparticles from the bottom surfaces of the septum 42a of the reagent bottles 30a during a cleaning process as shown in FIG. 12. The information may further indicate whether the reagent bottles 30a have been opened to avoid sending reagent bottles 30a which have already been opened through a cap cleaning process using the high-speed reagent bottle spinning device 92 as shown in FIG. 12.

The processor 19 of FIG. 1 is configured to sequentially activate the antennas 100 one-at-a-time to avoid receiving interference from other antennas 100 during a scan of the reagent cartridges 28 within the reagent manager 70. It is noted that the barcode reader 86 as shown in FIG. 11 is available to read the barcodes 62 of the reagent cartridges 28 in the event that the RFID devices 68 of the reagent cartridges 28 are unreadable. In this event, the antennas 100 may write the information from the barcodes 62 onto the RFID devices 68 of the reagent cartridges 28. Use of the antennas 100, the RFID devices 68, and the barcodes 62 allows the reagent manager 70 to perform faster inventory management.

Figure 16:
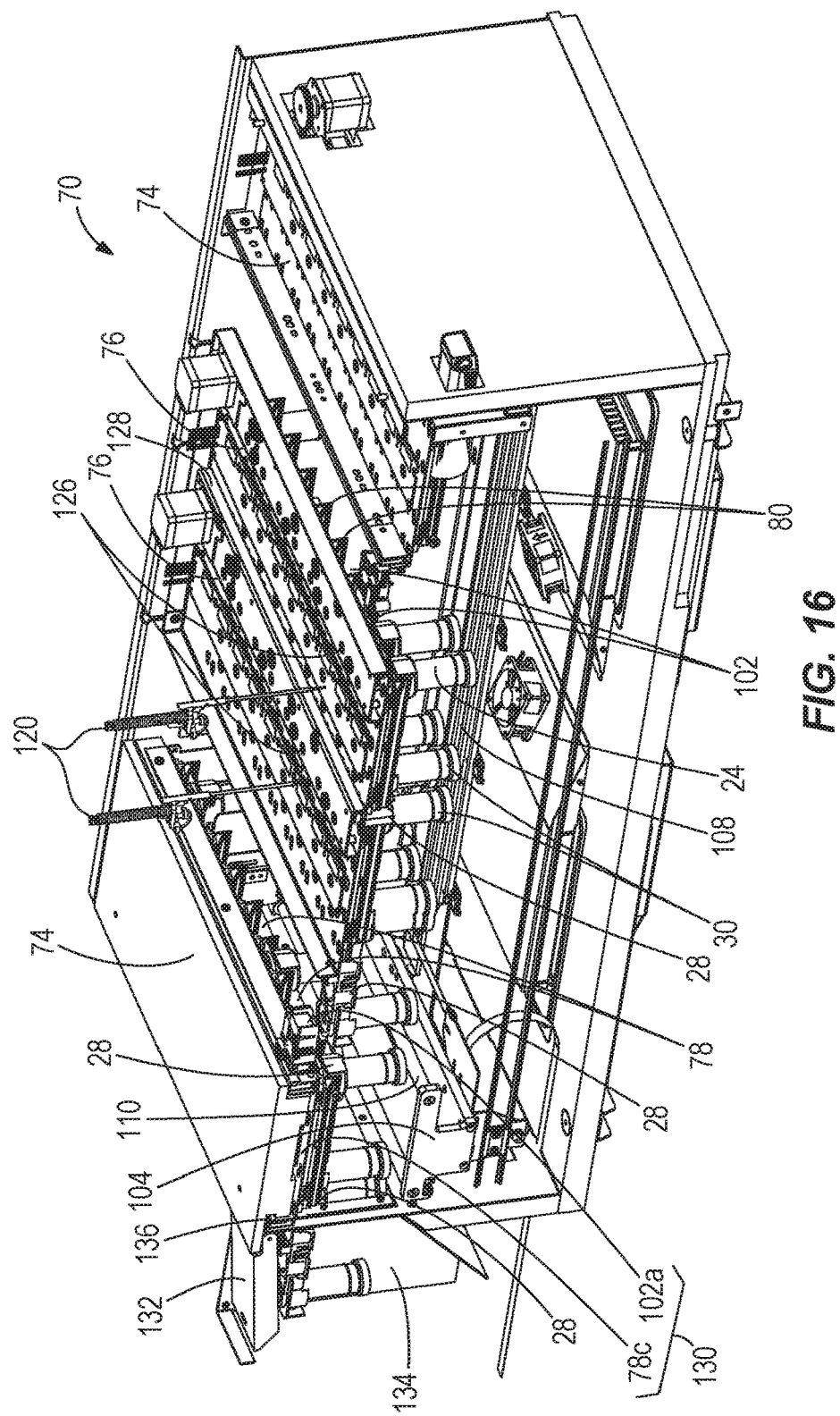
FIG. 16 illustrates a perspective view of the reagent manager of the embodiment of FIG. 9 with a back wall removed to illustrate a robot.
Figure 17:
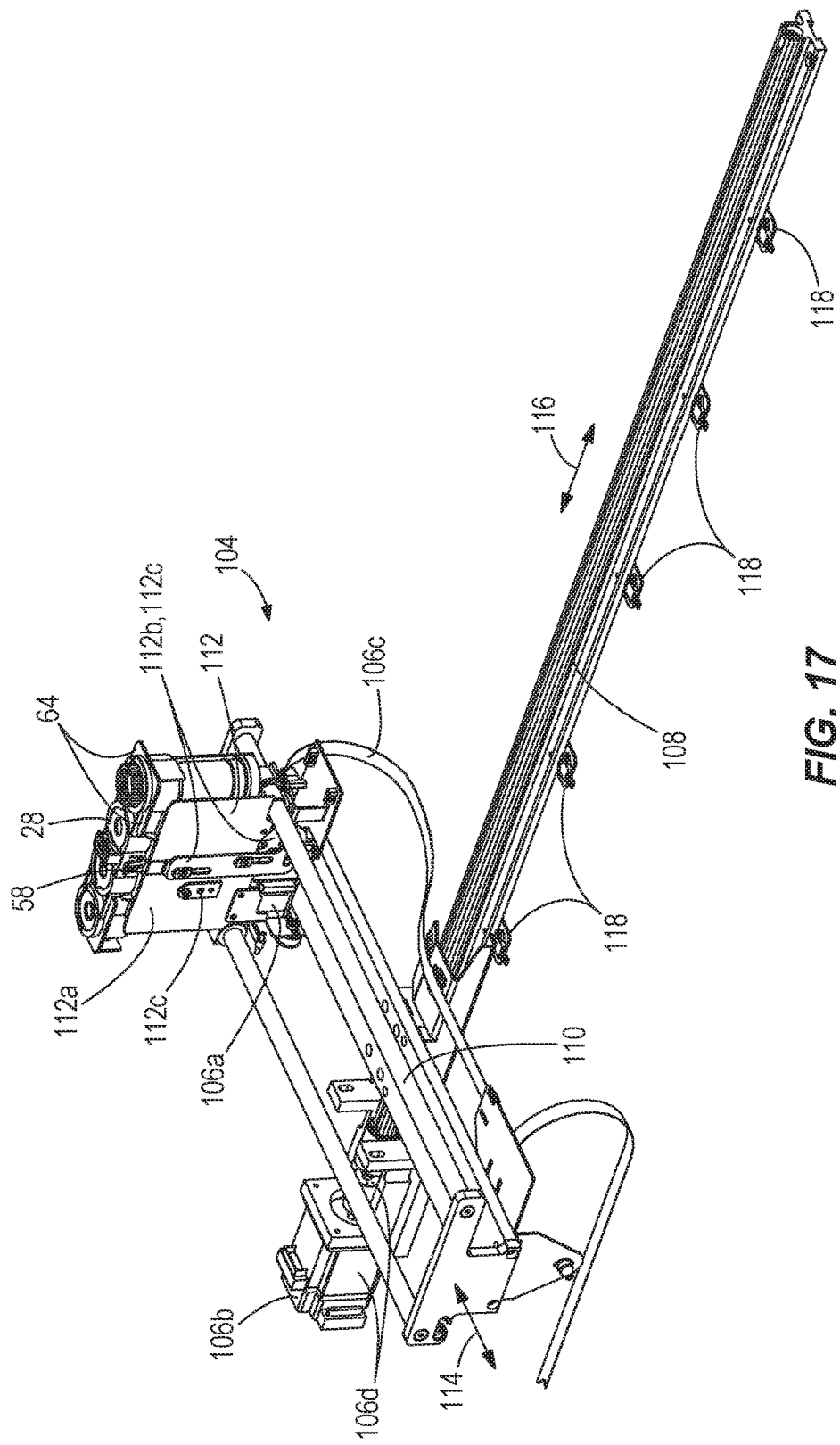
FIG. 17 illustrates a perspective view of the robot of FIG. 16 disposed outside of the reagent manager.

FIG. 16 illustrates a perspective view of the reagent manager 70 of the embodiment of FIG. 9 with a back wall removed to illustrate a robot 104. FIG. 17 illustrates a perspective view of the robot 104 of FIG. 16 outside of the reagent manager. The robot 104 of FIGS. 16 and 17 is configured to move the reagent cartridges 28 between the rows 78 and 102 of the storage areas 74 and operating areas 76 of the reagent manager 70, as shown in FIGS. 14 and 16, in order to position the reagent cartridges 28 in whichever locations are desired by the processor 19 of FIG. 1. The robot 104 contains motors 106a and 106b, an X-location member 108, a Y-location member 110, and a reagent cartridge carrying device 112. The reagent cartridge carrying device 112 contains sheet metal plates 112a to lift the reagent cartridges 28 and also contains a lever 112b which runs on an offset cam 112c to engage and disengage the spring member 58 of each of the reagent cartridges 28. This allows the robot 104 to unlock and lock the reagent cartridges 28 in a specific location in the rows 78 and 102 of the storage areas 74 and operating areas 76 of the reagent manager 70 as shown in FIGS. 14 and 16. The reagent cartridge carrying device 112 additionally contains an optical sensor 112c which detects the presence of a reagent cartridge 28 in a certain location of the rows 78 and 102 of the storage areas 74 and operating areas 76 of the reagent manager 70 as shown in FIGS. 14 and 16.

The motor 106a comprising an encoder enabled stepper motor and using a belt drive 106c moves the reagent cartridge carrying device 112 back and forth in directions 114 along the Y-location member 110 to control the orientation of the reagent cartridge carrying device 112 along directions 114. The motor 106b comprising an encoder enabled stepper motor and using a spline-shaft/leadscrew or a belt drive 106d moves the Y-location member 110 and the reagent cartridge carrying device 112 carried by the Y-location member 110 along the X-location member 108 back and forth in directions 116 to control the orientation of the reagent cartridge carrying device 112 along directions 116. In such manner, the reagent cartridge carrying device 112, which is configured to engage the reagent cartridges 28 one at a time, is configured to move the reagent cartridges 28 to anywhere within the reagent manager 70 of FIG. 16.

The X-location member 108 contains five hall-effect sensors 118 to detect the position of the Y-location member 110, and hence the position of the reagent cartridge carrying device 112, along the X-location member 108 in directions 116. This allows a determination to be made as to the exact X-location in direction 116 of the reagent cartridge carrying device 112 relative to the rows 78 and 102 of the storage areas 74 and operating areas 76 of the reagent manager 70 (as shown in FIGS. 14 and 16) based on which of the five hall effect sensors 118 are triggered by the Y-location member 110 as it moves along the X-location member 108.

The robot 104 is used to transfer the reagent cartridges 28 from the rows 78 of the closed storage drawers 72 of the storage area 74 to the rows 102 of the operating areas 76 as shown in FIGS. 14 and 16. The rail members 64 of each reagent cartridge 28 (shown in FIG. 17) slide into and along parallel and opposed mating guide members 80 (shown in FIG. 16) of each row 102 of the operating areas 76 in order to support the reagent cartridges 28 in the rows 102 of the operating areas 76. The spring member 58 (shown in FIG. 17) of each of the reagent cartridges 28 snaps into place within the pocket 90b (as shown in FIG. 11) of one of the opposed mating guide members 80 once each reagent cartridge 28 reaches it correct position thereby securing the reagent cartridge 28 in the correct position within the row 102 of the operating areas 76.

The robot 104 arranges the reagent cartridges 28 in an order to maximize throughput of the diagnostic analyzer 10 based on the assay panel size and configuration to be run. The robot 104 may place similar reagent cartridges 28 next to one another to allow a pipetting device (shown and discussed later) of the reagent manager 70 to access one type of reagent 24 from one reagent cartridge 28 and another type of reagent 24 from another reagent cartridge 28. The robot 104 may place up to sixteen reagent cartridges 28 collectively in the two operating areas 76 which allow the diagnostic analyzer 10 to run sixteen assay panels assuming that each assay requires only one reagent cartridge 28.

Figure 18:
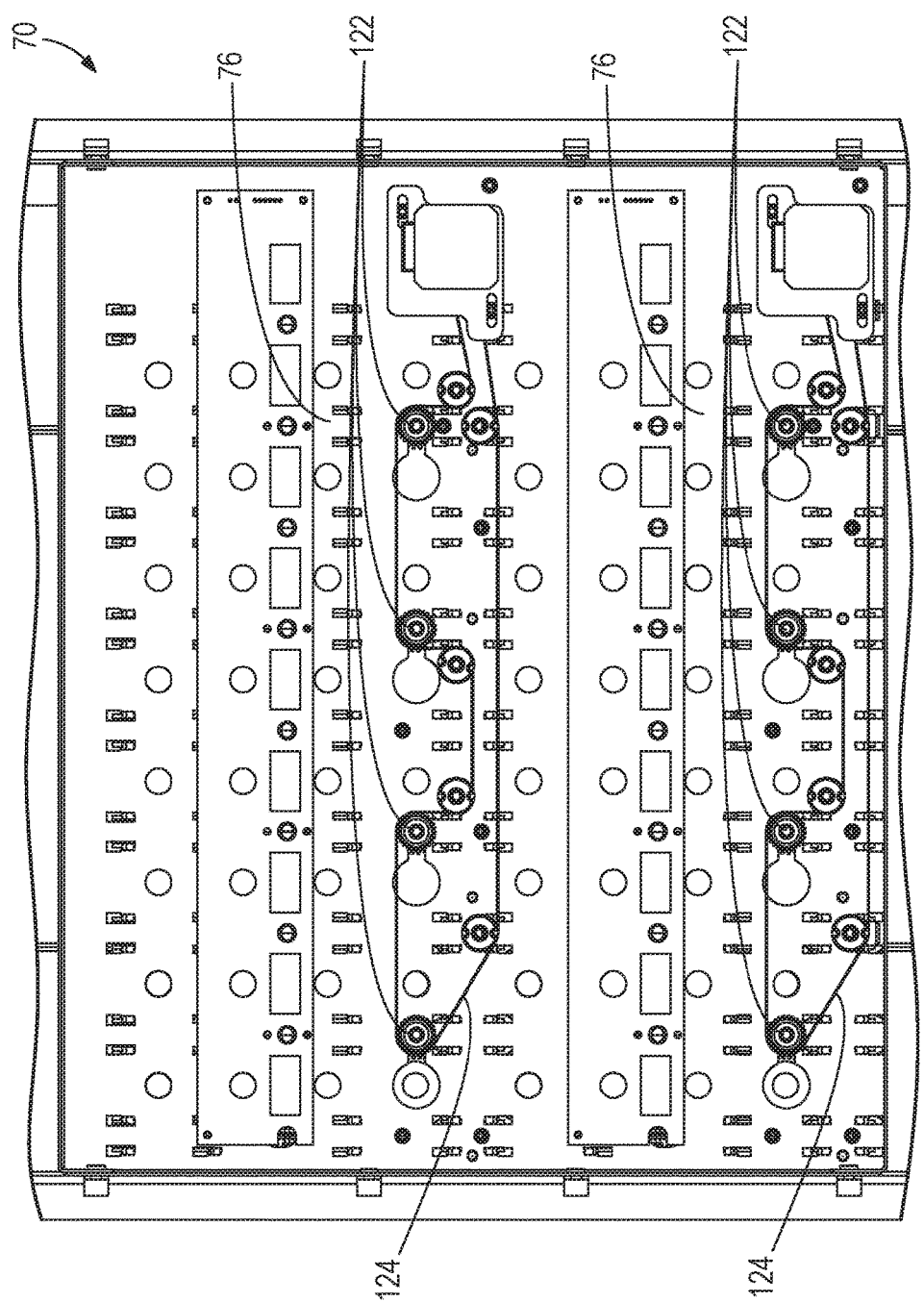
FIG. 18 illustrates a top view of the two operating areas of the reagent manager of the embodiment of FIG. 17 showing in each operating area a plurality of gears driven by a belt.
Figure 19:
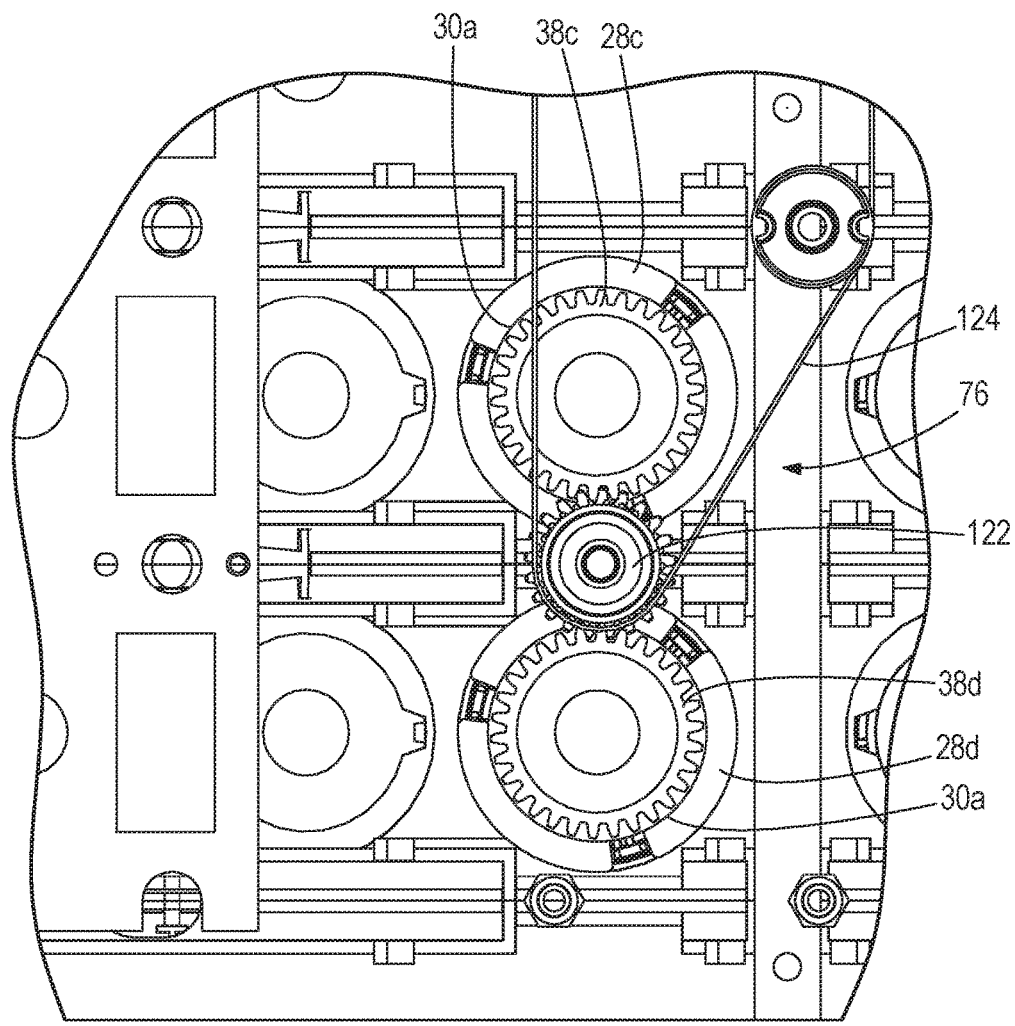
FIG. 19 illustrates a close-up view within a portion of one of the operating areas of the embodiment of FIG. 17 to show the belt driving the gears which drive dispersion gears of neighboring reagent cartridges.

FIG. 18 illustrates a top view of the two operating areas 76 of the reagent manager 70 of the embodiment of FIG. 17 showing in each operating area 76 a plurality of gears 122 driven by a belt 124. FIG. 19 illustrates a close-up view within a portion of one of the operating areas 76 of the embodiment of FIG. 17 to show the belt 124 driving the gears 122 which drive dispersion gears 38c and 38d of neighboring reagent cartridges 28c and 28d. Once the reagent cartridges 28c and 28d are locked in the correct locations within the rows 102 of the operating areas 76 as shown in FIG. 16, a motor (hidden from view) drives the belt 124 which drives the gears 122 which drives the dispersion gears 38c and 38d of the reagent cartridges 28c and 28d. It is noted that two reagent cartridges 28c and 28d may be driven by each of the gears 122. The belt 124 in each operating area 76 drives the gears 122 at a lower speed than the high-speed reagent bottle spinning device 92 of FIGS. 9 and 12 to provide a uniform flow of the reagent 24 within reagent bottle 30a.

As shown in FIG. 16, the pipetting device 120 may access and pipette out the reagent 24 in the reagent bottles 30 of the reagent cartridges 28 in the rows 102 of the operating areas 76 through holes 126 in the ceiling 128 of the operating areas 76. In such manner, the diagnostic analyzer system 10 of FIG. 1 may run an assay panel. While the pipetting device 120 is accessing the reagent 24 in the reagent bottles 30 of the reagent cartridges 28 in the rows 102 of the operating areas 76, the storage drawers 72 in the storage areas 74 of the reagent manager 70 may be opened and closed as shown in FIGS. 8 and 9 to add additional reagent cartridges 28 carrying reagent bottles 30 without disrupting/interfering with the pipetting device 120 thereby allowing for continuous processing.

As shown in FIG. 16, after the pipetting device 120 empties the reagent bottles 30 of the reagent 24, the robot 104 disposes the reagent cartridges 28 carrying the empty reagent bottles 30 in the aligned ninth and last waste row 102a of the operating areas 76. The aligned ninth and last waste rows 102a of the operating areas 76 is aligned with the ninth and last waste rows 78c of the storage areas 74 to form one continuous aligned waste row 130. After the reagent cartridges 28 carrying the empty reagent bottles 30 have been moved into the continuous aligned waste row 130 by the robot 104, the robot 104 pushes the reagent cartridges 28 in the continuous aligned waste row 130 against one another to push the reagent cartridges 28 against a passive waste door 132 which is aligned with the continuous aligned waste row 130. This pushing action forces the passive waste door 132 to open from a closed position at which point the robot 104 pushes the reagent cartridges 28 through the passive waste door 132 and out of the reagent manager housing 75 into a disposal device 134. Subsequently, a magnet and/or torsion spring 136 automatically closes the passive waste door 132 by magnetically biasing the passive waste door 132 back into the closed position. Use of the passive waste door 132 allows for the automated disposal of used reagent cartridges 28 which minimizes the user interaction and user handling time of manually unloading individual used reagent cartridges 28 and disposing of them without stopping assay processing.

In other embodiments, any of the components of the diagnostic analyzer system 10 of FIG. 1 including the reagent manager 70 of FIG. 8 may vary in number, type, configuration, or orientation, one or more of the components may be missing, or additional components may be added.

Figure 20:
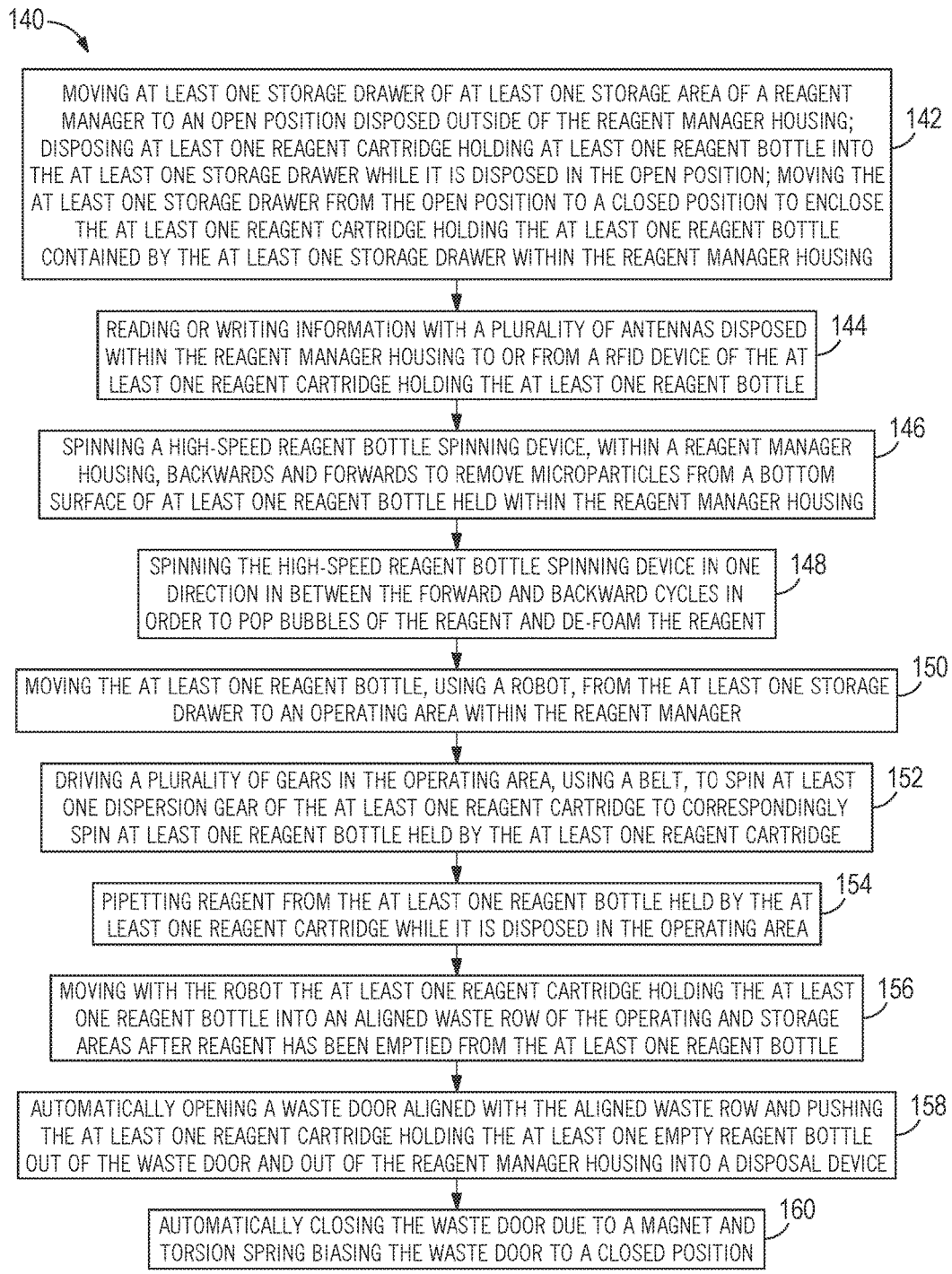
FIG. 20 is a flowchart illustrating one embodiment of a reagent manager of operating a reagent manager of a diagnostic analyzer system.

FIG. 20 illustrates one embodiment of a reagent manager 140 of operating a reagent manager of a diagnostic analyzer system. In step 142, the following may occur: at least one storage drawer of at least one storage area of a reagent manager may be moved to an open position disposed outside of the reagent manager housing; at least one reagent cartridge holding at least one reagent bottle may be disposed into the at least one storage drawer while it is disposed in the open position; and the at least one storage drawer may be moved from the open position to a closed position to enclose the at least one reagent cartridge holding the at least one reagent bottle contained by the at least one storage drawer within the reagent manager housing. The moving of the at least one storage drawer between the open and closed positions may not interfere with the processing of reagents in one or more operating areas allowing for continuous processing. The reagent manager may comprise a plurality of storage areas and a plurality of operating areas each having a plurality of rows which are each adapted to hold at least one reagent cartridge holding at least one reagent bottle. The reagent manager housing may be refrigerated.

In step 144, a plurality of antennas disposed within the reagent manager housing may read or write information to or from a RFID device of the at least one reagent cartridge holding the at least one reagent bottle. The information may comprise information such as test volume, number of days onboard, instrument identification on which the at least one reagent cartridge was used, or other pertinent information. The information may further comprise an indicator indicating whether the at least one reagent bottle held by the at least one reagent cartridge has been open or has been cleaned by a high-speed reagent bottle spinning device. The antennas may further determine a location and identification of the at least one cartridge within the reagent manager. Step 144 may further comprise a barcode reader of the reagent manager reading at least one barcode of the at least one reagent cartridge to determine information regarding the at least one reagent bottle held by the at least one reagent cartridge. The antennas may write information from the barcode of the at least one reagent cartridge to the RFID device of the at least one reagent cartridge.

In step 146, a high-speed reagent bottle spinning device, within a reagent manager housing, may be spun to remove microparticles from a bottom surface of at least one reagent bottle held within the reagent manager housing. This may result from the turbulent flow of reagent within the at least one reagent bottle which results from the high-speed spinning of the reagent bottle by the high-speed reagent bottle spinning device. The turbulent flow of reagent may splash against a septum of the at least one reagent bottle thereby removing the microparticles from the septum. The high-speed reagent bottle spinning device may be located in at least one storage area. This may be done using a motor which spins a plurality of gears which spin at least one dispersion gear of at least one reagent cartridge to spin one or more reagent bottles held by the at least one reagent cartridges. The at least one reagent bottle may comprise at least one fin disposed within the at least one reagent bottle which is disposed at an angle of 90 degrees. The at least one fin may further assist in creating the turbulent flow of the reagent towards and against the septum thereby removing the microparticles from the septum of the at least one reagent bottle. In one embodiment, step 146 may further comprise spinning the high-speed reagent bottle spinning device forward and backward at a rate to remove the microparticles from the bottom surface of the septum of the at least one reagent bottle held within the reagent manager housing. The high-speed reagent bottle spinning device may be spun forward and backward in a range of 40 to 80 forward and backward cycles. In a preferred embodiment, the high-speed reagent bottle spinning device may be spun forward and backward for 60 cycles for a total time of 35 to 45 seconds.

The spinning the high-speed reagent bottle spinning device forward may comprise the high-speed reagent bottle spinning device spinning forward to move reagent disposed within the at least one reagent bottle forward at a speed forward rate of between 5,000 degrees per second to 7,000 degrees per second, at an acceleration forward rate of between 110,000 degrees per second squared to 180,000 degrees per second squared, and at an angle of between 180 degrees to 360 degrees. In a preferred embodiment, the spinning the high-speed reagent bottle spinning device forward comprises the high-speed reagent bottle spinning device spinning forward to move reagent disposed within the at least one reagent bottle forward at a speed forward rate of 5,625 degrees per second, at an acceleration forward rate of 135,000 degrees per second squared, and at an angle of 281 degrees.

The spinning the high-speed reagent bottle spinning device backward may comprise the high-speed reagent bottle spinning device spinning backward to move reagent disposed within the at least one reagent bottle backward at a speed backward rate of between 5,000 degrees per second to 7,000 degrees per second, at an acceleration backward rate of between 110,000 degrees per second squared to 180,000 degrees per second squared, and at an angle of between 180 degrees to 360 degrees. In a preferred embodiment, the spinning the high-speed reagent bottle spinning device backward comprises the high-speed reagent bottle spinning device spinning backward to move reagent disposed within the at least one reagent bottle backward at a speed backward rate of 5,625 degrees per second, at an acceleration backward rate of 135,000 degrees per second squared, and at an angle of 281 degrees.

Step 146 may further comprise having a delay in a range of between 250 milliseconds to 750 milliseconds after both the forward and backward spinning. In a preferred embodiment, the delay after both the forward and backward spinning of the reagent bottles is 500 milliseconds.

In step 148, the high-speed reagent bottle spinning device may be spun in one direction in between the forward and backward cycles in order to pop bottles of the reagent and de-foam the reagent. This anti-foam movement may comprise any of the embodiments disclosed herein.

In step 150, the at least one reagent bottle may be moved, using a robot, from the at least one storage drawer in the closed position to an operating area within the reagent manager. In step 152, a belt may drive a plurality of gears in the operating area which may spin at least one dispersion gear of at least one reagent cartridge to correspondingly spin at least one reagent bottle held by the at least one reagent cartridge. In step 154, reagent may be pipetted from the at least one reagent bottle held by the at least one reagent cartridge while it is disposed in the operating area.

In step 156, the at least one reagent cartridge holding the at least one reagent bottle may be moved using the robot into an aligned waste row of the operating and storage areas after reagent has been emptied from the at least one reagent bottle. In step 158, a waste door aligned with the aligned waste row may be automatically opened and the at least one reagent cartridge holding the at least one empty reagent bottle may be pushed out of the waste door and out of the reagent manager housing into a disposal device. In step 160, the waste door may automatically close due to a magnet and torsion spring biasing the waste door to a closed position.

One or more embodiments of the disclosure may reduce one or more issues of one or more of the existing diagnostic analyzer systems. For instance, the reagent manager 70 of the disclosure may provide a continuous supply of reagents 24 to the diagnostic analyzer system 10 for assay processing and may allow users to load reagent cartridges 28 in random order without disrupting assay processing. It also may automatically clean the septum 42 of the reagent bottles 30 of microparticles to avoid the user from having to spend a great deal of time preparing and shaking the reagent bottles 30 prior to insertion into the reagent manager 70. Additionally, it may ensure that the reagents 24 are maintained at two to twelve degrees Celsius. Further, it may automatically dispose of the used reagent cartridges 28. Finally, it may provide enough capacity to support up to twenty-five hours of walkaway time (calculated based on five-hundred test kits), and may increase through-put and time efficiency due to the smart placement of reagent cartridges 28 into the appropriate locations and the quick location and identification of reagent cartridges 28 within the reagent manager 70 as a result of the use of RFID devices 68, antennas 100, and barcodes 62.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This reagent manager of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A reagent manager for a diagnostic analyzer system comprising:
   a reagent manager housing containing a reagent bottle having microparticles accumulated to an inner surface of a septum, the inner surface configured to allow a pipetting device of the diagnostic analyzer system to access within the reagent bottle, and having liquid disposed within the reagent bottle;
   a first spinning device, comprising a first gear, disposed within the reagent manager housing;
   a second spinning device, comprising a second gear, disposed within the reagent manager housing;
   a processor in electronic communication with the first and second spinning devices; and
   a memory in electronic communication with the processor, wherein the memory comprises programming code for execution by the processor, and the programming code is configured to control the first spinning device so that the first gear spins the reagent bottle, around an axis through the reagent bottle, at a first speed in a plurality of cycles thereby causing a turbulent flow of the liquid within the reagent bottle causing the liquid to contact and remove the microparticles from the inner surface of the septum of the reagent bottle, and to subsequently control the second spinning device so that the second gear spins the reagent bottle, around the axis through the reagent bottle, at a second speed, lower than the first speed, to disperse the microparticles, removed from the inner surface of the septum, within the liquid disposed within the reagent bottle.

2. The reagent manager of claim 1 wherein the programming code is configured to control the first spinning device so that the first gear spins the reagent bottle clockwise and counter-clockwise to move the liquid disposed within the reagent bottle clockwise and counter-clockwise at a speed rate of between 5,000 degrees per second to 7,000 degrees per second, at an acceleration rate of between 110,000 degrees per second squared to 180,000 degrees per second squared, and in a rotation of between 180 degrees to 360 degrees.

3. The reagent manager of claim 1 wherein the programming code is configured to control the first spinning device so that there is a delay in a range of between 250 milliseconds to 750 milliseconds in-between clockwise and counter-clockwise cycles of the first gear.

4. The reagent manager of claim 1 wherein the programming code is configured to control the first spinning device so that the first gear spins the reagent bottle in a range of 40 to 80 clockwise and counter-clockwise cycles.

5. The reagent manager of claim 1 wherein the reagent bottle comprises at least one fin disposed within the reagent bottle, the at least one fin disposed at an angle of 90 degrees relative to an outer surface of the reagent bottle.

6. The reagent manager of claim 1 wherein the reagent bottle comprises two fins disposed within the reagent bottle, the two fins disposed at an angle of 90 degrees relative to an outer surface of the reagent bottle.

7. The reagent manager of claim 1 wherein the programming code is configured to control the first spinning device so that the first gear spins the reagent bottle, in between a first set of clockwise and counter-clockwise cycles, in a first number of consecutive, plural one-directional rotations to de-foam the liquid, and so that the first gear spins the reagent bottle, in between a second set of clockwise and counter-clockwise cycles, in a second number of consecutive, plural one-directional rotations, different than the first number, to de-foam the liquid.

8. The reagent manager of claim 1 wherein the first gear of the first spinning device is disposed at a first location of the reagent manager housing, and the second gear of the second spinning device is located at a second location of the reagent manager housing.

9. The reagent manager of claim 2 wherein the programming code is configured to control the first spinning device so that the first gear spins the reagent bottle in a range of 40 to 80 clockwise and counter-clockwise cycles.

10. The reagent manager of claim 9 wherein the programming code is configured to control the first spinning device so that there is a delay in a range of between 250 milliseconds to 750 milliseconds in-between clockwise and the counter-clockwise cycles of the first gear.

11. The reagent manager of claim 1 further comprising a reagent cartridge holding the reagent bottle within the reagent manager housing.

12. The reagent manager of claim 11 wherein the programming code is configured to control the first spinning device so that the first gear spins the reagent bottle relative to the reagent cartridge at the first speed, and to control the second spinning device so that the second gear spins the reagent bottle relative to the reagent cartridge at the second speed.

13. The reagent manager of claim 12 wherein the reagent cartridge comprises a dispersion gear, and the programming code is configured to control the first spinning device so that the first gear rotates the dispersion gear of the reagent cartridge which in turn rotates the reagent bottle held by the reagent cartridge, and to control the second spinning device so that the second gear rotates the dispersion gear of the reagent cartridge which in turn rotates the reagent bottle held by the reagent cartridge.

14. The reagent manager of claim 8 further comprising a robot, wherein the programming code is configured to control the robot to move the reagent bottle between the first location and the second location of the reagent manager housing.

15. The reagent manager of claim 1 wherein the first spinning device comprises a first gear chain of gears, and the programming code is configured to control the first spinning device to spin the first gear chain of gears.

16. The reagent manager of claim 15 wherein the reagent manager housing contains a plurality of reagent bottles each containing liquid and each having microparticles attached to an inner surface of their respective septum, and the programming code is configured to control the first spinning device to spin the first gear chain of gears to spin the reagent bottles, around axis through each of the reagent bottles, at the first speed in the plurality of cycles thereby causing the turbulent flow of the liquid within the reagent bottles causing the liquid to contact and remove the microparticles from the inner surface of each respective septum of the reagent bottles.

17. The reagent manager of claim 16 further comprising a plurality of reagent cartridges holding the reagent bottles within the reagent manager housing, each of the the reagent cartridges comprising a respective dispersion gear, wherein the programming code is configured to control the first spinning device so that the first gear chain of gears rotates the respective dispersion gear of each of the reagent cartridges which in turn rotates the reagent bottles held by the reagent cartridges.

18. The reagent manager of claim 17 wherein the second spinning device comprises a second gear chain of gears, and the programming code is configured to control the second spinning device to spin the second gear chain of gears.

19. The reagent manager of claim 18 wherein the programming code is configured to control the second spinning device to spin the second gear chain of gears to spin the reagent bottles, around axis through each of the reagent bottles, at the second speed to disperse the microparticles, removed from the inner surface of the respective septum of each of the reagent bottles, within the liquid disposed within the reagent bottles.

20. The reagent manager of claim 19 wherein the programming code is configured to control the second spinning device so that the second gear chain of gears rotates the respective dispersion gear of each of the reagent cartridges which in turn rotates the reagent bottles held by the reagent cartridges.

* * * * *